(12) United States Patent
Sunstrom

(10) Patent No.: US 9,404,078 B2
(45) Date of Patent: Aug. 2, 2016

(54) CELL EXPRESSION SYSTEM

(71) Applicant: NeuClone Biologics Pty Ltd, Eveleigh, New South Wales (AU)

(72) Inventor: Noelle Sunstrom, Eveleigh (AU)

(73) Assignee: NeuClone Biologics Pty Ltd, Eveleigh, NSW (AU)

(*) Notice: Subject to any disclaimer, the term of this patent is extended or adjusted under 35 U.S.C. 154(b) by 0 days.

(21) Appl. No.: 14/773,287

(22) PCT Filed: Feb. 17, 2014

(86) PCT No.: PCT/AU2014/000129
§ 371 (c)(1),
(2) Date: Sep. 4, 2015

(87) PCT Pub. No.: WO2014/134657
PCT Pub. Date: Sep. 12, 2014

(65) Prior Publication Data
US 2016/0017281 A1    Jan. 21, 2016

(30) Foreign Application Priority Data

Mar. 8, 2013  (AU) ............................... 2013900804
Mar. 8, 2013  (AU) ............................... 2013900808

(51) Int. Cl.
| | |
|---|---|
| *C12N 15/67* | (2006.01) |
| *C12N 15/85* | (2006.01) |
| *C07K 14/61* | (2006.01) |
| *C12N 5/073* | (2010.01) |
| *C07K 16/24* | (2006.01) |
| *C12N 9/06* | (2006.01) |

(52) U.S. Cl.
CPC .............. *C12N 5/0605* (2013.01); *C07K 14/61* (2013.01); *C07K 16/241* (2013.01); *C12N 15/67* (2013.01); *C12N 15/85* (2013.01); *C07K 2317/14* (2013.01); *C12N 9/003* (2013.01); *C12N 2510/02* (2013.01)

(58) Field of Classification Search
CPC ...... C12N 5/0605; C12N 15/67; C12N 9/003; C12N 15/85; C12N 2510/02; C07K 14/61; C07K 2317/14
See application file for complete search history.

(56) References Cited

FOREIGN PATENT DOCUMENTS

| | | | |
|---|---|---|---|
| KR | 772031 | * | 10/2007 |
| WO | 02/46430 | | 6/2002 |
| WO | 03106658 | | 12/2003 |
| WO | 03/046162 | | 6/2006 |

OTHER PUBLICATIONS

Sunstrom, N.A., et al., "Regulated autocrine growth of CHO cells", Cytotechnology, 2000, 34:39-46.
Hunt, S.M.N., et al., "Chinese hamster ovary cells produce sufficient recombinant insulin-like growth factor I to support growth in serum-free medium", Cytotechnology, 1997, 24:55-64.
Cacciatore, J.J., et al., "Gene amplification and vector engineering to achieve rapid and high-level therapeutic protein production using the Dhfr-based CHO cell selection system", Biotechnology Advances, 2010, 28:673-681.
Zhu, J., "Mammalian cell protein expression for biopharmaceutical production", Biotechnology Advances, 2012, 30:1158-1170.
Kuhlmann, M & Covic, A., "The protein science of biosimilars", Nephrology Dialysis Transplantation, 2006, 21 (Suppl 5):v4-v8.
Ho, Steven CL, et al., "Generation of monoclonal antibody-producing mammalian cell lines", 2013, Pharm. Bioprocess., 1(1):71-87.

* cited by examiner

*Primary Examiner* — Daniel C Gamett
(74) *Attorney, Agent, or Firm* — Michael B. Rubin; Bozicevic, Field & Francis LLP

(57) ABSTRACT

An expression system for expressing a protein comprising: a eukaryotic host cell carrying a dihydrofolate reductase (DHFR) deficiency; and an expression vector, the expression vector encoding the human growth hormone gene; a expression vector, the expression vector comprising: a eukaryotic selectable marker including a minimal SV 40 early promoter driving expression of a sequence encoding dihydrofolate reductase for complementing the DHFR deficiency in the host cell; a prokaryotic selectable marker conveying Ampicillin resistance to a prokaryotic host cell; a prokaryotic Origin of Replication; a plurality of multiple cloning sites (MCS); and at least one protein expression module comprising: a Simian Vacuolating Virus 40 (SV40) early promoter, inclusive of its 72 bp enhancer repeats; and a rabbit β-globin intron sequence being separable from a SV40 p A sequence by a first multiple cloning site, for receiving a coding sequence and expressing a desired protein therefrom.

19 Claims, 11 Drawing Sheets

SEQUENCE LISTING

<160> NUMBER OF SEQ ID NOS: 8

<210> SEQ ID NO 1
<211> LENGTH: 4183
<212> TYPE: DNA
<213> ORGANISM: Artificial Sequence
<220> FEATURE:
<223> OTHER INFORMATION: Synthetic oligonucleotide

<400> SEQUENCE: 1

```
ccggtctagt taactagcac cgatatcaat gaatgcaatt gttgttgtta acttgtttat      60
tgcagcttat aatggttaca aataaagcaa tagcatcaca aatttcacaa ataaagcatt     120
tttttcactg cattctagtt gtggtttgtc caaactcatc aatgtatctt atcatgtctg     180
aattcgtaat catggtcata gctgtttcct gtgtgaaatt gttatccgct cacaattcca     240
cacaacatac gagccggaag cataaagtgt aaagcctggg gtgcctaatg agtgagctaa     300
ctcacattaa ttgcgttgcg ctcactgccc gctttccagt cgggaaacct gtcgtgccag     360
ctgcattaat gaatcggcca acgcgcgggg agaggcggtt tgcgtattgg gcgctcttcc     420
gcttcctcgc tcactgactc gctgcgctcg tcgttcggc tgcggcgagc ggtatcagct      480
cactcaaagg cggtaatacg gttatccaca gaatcagggg ataacgcagg aaagaacatg     540
tgagcaaaag gccagcaaaa ggccaggaac cgtaaaaagg ccgcgttgct ggcgtttttc     600
cataggctcc gcccccctga cgagcatcac aaaaatcgac gctcaagtca gaggtggcga     660
aacccgacag gactataaag ataccaggcg tttccccctg gaagctccct cgtgcgctct     720
cctgttccga ccctgccgct taccggatac ctgtccgcct ttctcccttc gggaagcgtg     780
gcgctttctc atagctcacg ctgtaggtat ctcagttcgg tgtaggtcgt tcgctccaag     840
ctgggctgtg tgcacgaacc ccccgttcag cccgaccgct gcgccttatc cggtaactat     900
cgtcttgagt ccaacccggt aagacacgac ttatcgccac tggcagcagc cactggtaac     960
aggattagca gagcgaggta tgtaggcggt gctacagagt tcttgaagtg gtggcctaac    1020
tacggctaca ctagaaggac agtatttggt atctgcgctc tgctgaagcc agttaccttc    1080
ggaaaaagag ttggtagctc ttgatccggc aaacaaacca ccgctggtag cggtggtttt    1140
tttgtttgca agcagcagat tacgcgcaga aaaaaggat ctcaagaaga tcctttgatc    1200
ttttctacgg ggtctgacgc tcagtggaac gaaaactcac gttaagggat tttggtcatg    1260
agattatcaa aaaggatctt cacctagatc ctttaaatt aaaaatgaag ttttaaatca    1320
```

```
atctaaagta tatatgagta aacttggtct gacagttacc aatgcttaat cagtgaggca    1380
cctatctcag cgatctgtct atttcgttca tccatagttg cctgactccc cgtcgtgtag    1440
ataactacga tacgggaggg cttaccatct ggccccagtg ctgcaatgat accgcgagac    1500
ccacgctcac cggctccaga tttatcagca ataaaccagc cagccggaag ggccgagcgc    1560
agaagtggtc ctgcaacttt atccgcctcc atccagtcta ttaattgttg ccgggaagct    1620
agagtaagta gttcgccagt taatagtttg cgcaacgttg ttgccattgc tacaggcatc    1680
gtggtgtcac gctcgtcgtt tggtatggct tcattcagct ccggttccca acgatcaagg    1740
cgagttacat gatccccat gttgtgcaaa aaagcggtta gctccttcgg tcctccgatc    1800
gttgtcagaa gtaagttggc cgcagtgtta tcactcatgg ttatggcagc actgcataat    1860
tctcttactg tcatgccatc cgtaagatgc ttttctgtga ctggtgagta ctcaaccaag    1920
tcattctgag aatagtgtat gcggcgaccg agttgctctt gcccggcgtc aatacgggat    1980
aataccgcgc cacatagcag aactttaaaa gtgctcatca ttggaaaacg ttcttcgggg    2040
cgaaaactct caaggatctt accgctgttg agatccagtt cgatgtaacc cactcgtgca    2100
cccaactgat cttcagcatc ttttactttc accagcgttt ctgggtgagc aaaaacagga    2160
aggcaaaatg ccgcaaaaaa gggaataagg gcgacacgga aatgttgaat actcatactc    2220
ttcctttttc aatattattg aagcatttat cagggttatt gtctcatgag cggatacata    2280
tttgaatgta tttagaaaaa taaacaaata ggggttccgc gcacatttcc ccgaaaagtg    2340
ccacctgacg tccacacaaa aaccaacac acagatgtaa tgaaaataaa gatattttat    2400
tgcggccatc gtgatggcag gttgggcgtc gcttggtcgg tcatttcgaa ccccagagtc    2460
ccgctcagaa gaactcgtca agaaggcgat agaaggcgat gcgctgcgaa tcgggagcgg    2520
cgataccgta aagcacgagg aagcggtcag cccattcgcc gccaagctct tcagcaatat    2580
cacgggtagc caacgctatg tcctgatagc ggtccgccac acccagccgg ccacagtcga    2640
tgaatccaga aaagcggcca ttttccacca tgatattcgg caagcaggca tcgccatggg    2700
tcacgacgag atcctcgccg tcgggcatgc gcgccttgag cctggcgaac agttcggctg    2760
gcgcgagccc ctgatgctct tcgtccagat catcctgatc gacaagaccg gcttccatcc    2820
gagtacgtgc tcgctcgatg cgatgtttcg cttggtggtc gaatgggcag gtagccggat    2880
caagcgtatg cagccgccgc attgcatcag ccatgatgga tactttctcg gcaggagcaa    2940
ggtgagatga caggagatcc tgccccggca cttcgcccaa tagcagccag tcccttcccg    3000
cttcagtgac aacgtcgagc acagctgcgc aaggaacgcc cgtcgtggcc agccacgata    3060
gccgcgctgc ctcgtcctgc agttcattca gggcaccgga caggtcggtc ttgacaaaaa    3120
gaaccgggcg cccctgcgct gacagccgga acacggcggc atcagagcag ccgattgtct    3180
gttgtgccca gtcatagccg aatagcctct ccacccaagc ggccggagaa cctgcgtgca    3240
atccatcttg ttcaatcata gctcagaggc cgaggcggcc tcggcctctg cataaataaa    3300
aaaaattagt cagccatggg gcggagaatg ggcggaactg gcggagctc agaggccgag    3360 gcggcctcgg cctctgcata aataaaaaaa attagtcagc catgggcgg agaatgggcg    3420 gaactgggcg ggatcctca atattggcca ttagccatat tattcattgg ttatatagca    3480
taaatcaata ttggctattg gccattgcat acgttgtatc tatatcataa tatgtacatt    3540
tatattggct catgtccaat atgaccgcca tgttggcatt gattattgac tagttattaa    3600
tagtaatcaa ttacggggtc attagttcat agcccatata tggagttccg cgttacataa    3660
cttacggtaa atggcccgcc tggctgaccg cccaacgacc cccgcccatt gacgtcaata    3720
```

| atgacgtatg | ttcccatagt | aacgccaata | gggactttcc | attgacgtca | atgggtggag | 3780 |
| tatttacggt | aaactgccca | cttggcagta | catcaagtgt | atcatatgcc | aagtccgccc | 3840 |
| cctattgacg | tcaatgacgg | taaatggccc | gcctggcatt | atgcccagta | catgacctta | 3900 |
| cgggactttc | ctacttggca | gtacatctac | gtattagtca | tcgctattac | catggtgatg | 3960 |
| cggttttggc | agtacaccaa | tgggcgtgga | tagcggtttg | actcacgggg | atttccaagt | 4020 |
| ctccacccca | ttgacgtcaa | tgggagtttg | ttttggcacc | aaaatcaacg | ggactttcca | 4080 |
| aaatgtcgta | ataaccccgc | cccgttgacg | caaatgggcg | gtaggcgtgt | acggtgggag | 4140 |
| gtctatataa | gcagagctcg | tttagtgaac | cgtcagatca | aaa | | 4183 |

<210> SEQ ID NO 2
<211> LENGTH: 5122
<212> TYPE: DNA
<213> ORGANISM: Artificial Sequence
<220> FEATURE:
<223> OTHER INFORMATION: Synthetic oligonucleotide

<400> SEQUENCE: 2

| gatcccgggc | gcagcaccat | ggcctgaaat | aacctctgaa | agaggaactt | ggttaggtac | 60 |
| cttctgaggc | ggaaagaacc | agctgtggaa | tgtgtgtcag | ttagggtgtg | gaaagtcccc | 120 |
| aggctcccca | gcaggcagaa | gtatgcaaag | catgcatctc | aattagtcag | caaccaggtg | 180 |
| tggaaagtcc | ccaggctccc | cagcaggcag | aagtatgcaa | agcatgcatc | tcaattagtc | 240 |
| agcaaccata | gtcccgcccc | taactccgcc | catcccgccc | ctaactccgc | ccagttccgc | 300 |
| ccattctccg | ccccatggct | gactaatttt | ttttatttat | gcagaggccg | aggccgcctc | 360 |
| ggcctctgag | ctattccaga | agtagtgagg | aggcttttt | ggaggcctag | gcttttgcaa | 420 |
| aaagctgatc | ctgagaactt | cagggtgagt | ttggggaccc | ttgattgttc | tttctttttc | 480 |
| gctattgtaa | aattcatgtt | atatggaggg | ggcaaagttt | tcagggtgtt | gtttagaatg | 540 |
| ggaagatgtc | ccttgtatca | ccatggaccc | tcatgataat | tttgtttctt | tcactttcta | 600 |
| ctctgttgac | aaccattgtc | tcctcttatt | ttcttttcat | tttctgtaac | ttttcgtta | 660 |
| aactttagct | tgcatttgta | acgaattttt | aaattcactt | ttgtttattt | gtcagattgt | 720 |
| aagtactttc | tctaatcact | ttttttttcaa | ggcaatcagg | gtatattata | ttgtacttca | 780 |
| gcacagtttt | agagaacaat | tgttataatt | aaatgataag | gtagaatatt | tctgcatata | 840 |
| aattctggct | ggcgtggaaa | tattcttatt | ggtagaaaca | actacatcct | ggtcatcatc | 900 |
| ctgcctttct | ctttatggtt | acaatgatat | acactgtttg | agatgaggat | aaaatactct | 960 |
| gagtccaaac | cgggcccctc | tgctaaccat | gttcatgcct | tcttcttttt | cctacagctc | 1020 |
| ctgggcaacg | tgctggttgt | tgtgctgtct | catcattttg | gcaaagcgcg | ttaacgttac | 1080 |
| tggccgaagc | cgcttggaat | aaggccggtg | tgcgtttgtc | tatatgtgat | tttccaccat | 1140 |
| attgccgtct | tttggcaatg | tgagggcccg | gaaacctggc | cctgtcttct | tgacgagcat | 1200 |
| tcctaggggt | ctttcccctc | tcgccaaagg | aatgcaaggt | ctgttgaatg | tcgtgaagga | 1260 |
| agcagttcct | ctggaagctt | cttgaagaca | aacaacgtct | gtagcgaccc | tttgcaggca | 1320 |
| gcggaacccc | ccacctggcg | acaggtgcct | ctgcggccaa | aagccacgtg | tataagatac | 1380 |
| acctgcaaag | gcggcacaac | cccagtgcca | cgttgtgagt | tggatagttg | tggaaagagt | 1440 |
| caaatggctc | tcctcaagcg | tattcaacaa | ggggctgaag | gatgcccaga | aggtacccca | 1500 |
| ttgtatggga | tctgatctgg | ggcctcggtg | cacatgcttt | acatgtgttt | agtcgaggtt | 1560 |

```
aaaaaaacgt ctaggccccc cgaaccacgg ggacgtggtt ttcctttgaa aaacacgatg    1620
ataatcgatg gcaatcctag cgtgaaggct ggtaggattt tatccccgct gccatcatgg    1680
ttcgaccatt gaactgcatc gtcgccgtgt cccaaaatat ggggattggc aagaacggag    1740
acctaccctg gcctccgctc aggaacgagt tcaagtactc ccaaagaatg accacaacct    1800
cttcagtgga aggtaaacag aatctggtga ttatgggtag gaaaacctgg ttctccattc    1860
ctgagaagaa tcgacccttta aaggacagaa ttaatatagt tctcagtaga gaactcaaag    1920
aaccaccacg aggagctcat tttcttgcca aaagtttgga tgatgcctta agacttattg    1980
aacaaccgga attggcaagt aaagtagaca tggtttggat agtcggaggc agttctgttt    2040
accaggaagc catgaatcaa ccaggccacc tcagactctt tgtgacaagg atcatgcagg    2100
aatttgaaag tgacacgttt ttcccagaaa ttgatttggg gaaatataaa ctttctcccag   2160 aatacccagg cgtcctctct gaggtccagg aggaaaaagg catcaagtat aagtttgaag    2220
tctacgagaa gaaagactaa caggaagatg ctttcaagtt ctctgctccc ctcctaaagc    2280
tatgcatttt tataagacca tgggacttttt gctggcttta gatcctcgag aatgaatgca    2340
attgttgttg ttaacttgtt tattgcagct tataatggtt acaaataaag caatagcatc    2400
acaaatttca caaataaagc attttttttca ctgcattcta gttgtggttt gtccaaactc    2460
atcaatgtat cttatcatgt ctggataagc ttggcactgg ccgtcgtttt acaacgtcgt    2520
gactgggaaa accctggcgt tacccaactt aatcgccttg cagcacatcc ccctttcgcc    2580
agctggcgta atagcgaaga ggcccgcacc gatcgccctt cccaacagtt gcgcagcctg    2640
aatggcgaat ggcgcctgat gcggtatttt ctccttacgc atctgtgcgg tatttcacac    2700
cgcatatggt gcactctcag tacaatctgc tctgatgccg catagttaag ccagccccga    2760
cacccgccaa cacccgctga cgcgccctga cgggcttgtc tgctcccggc atccgcttac    2820
agacaagctg tgaccgtctc cgggagctgc atgtgtcaga ggttttcacc gtcatcaccg    2880
aaacgcgcga gacgaaaggg cctcgtgata cgcctatttt tataggttaa tgtcatgata    2940
ataatggttt cttagacgtc aggtggcact tttcggggaa atgtgcgcgg aaccccta tt    3000 tgtttatttt tctaaataca ttcaaatatg tatccgctca tgagacaata accctgataa    3060
atgcttcaat aatattgaaa aaggaagagt atgagtattc aacatttccg tgtcgccctt    3120 attcccttttt ttgcggcatt ttgccttcct gttttttgctc acccagaaac gctggtgaaa    3180
gtaaaagatg ctgaagatca gttgggtgca cgagtgggtt acatcgaact ggatctcaac    3240
agcggtaaga tccttgagag ttttcgcccc gaagaacgtt ttccaatgat gagcactttt    3300
aaagttctgc tatgtggcgc ggtattatcc cgtattgacg ccgggcaaga gcaactcggt    3360
cgccgcatac actattctca gaatgacttg gttgagtact caccagtcac agaaaagcat    3420
cttacggatg gcatgacagt aagagaatta tgcagtgctg ccataaccat gagtgataac    3480
actgcggcca acttacttct gacaacgatc ggaggaccga aggagctaac cgcttttttg    3540
cacaacatgg gggatcatgt aactcgcctt gatcgttggg aaccggagct gaatgaagcc    3600
ataccaaacg acgagcgtga caccacgatg cctgtagcaa tggcaacaac gttgcgcaaa    3660
ctattaactg gcgaactact tactctagct tcccggcaac aattaataga ctggatggag    3720
gcggataaag ttgcaggacc acttctgcgc tcggcccttc cggctggctg gtttattgct    3780
gataaatctg gagccggtga gcgtgggtct cgcggtatca ttgcagcact ggggccagat    3840
ggtaagccct cccgtatcgt agttatctac acgacgggga gtcaggcaac tatggatgaa    3900
cgaaatagac agatcgctga gataggtgcc tcactgatta agcattggta actgtcagac    3960
```

```
caagtttact catatatact ttagattgat ttaaaacttc attttttaatt taaaaggatc    4020 taggtgaaga tccttttttga taatctcatg accaaaatcc cttaacgtga gttttcgttc    4080
cactgagcgt cagaccccgt agaaaagatc aaaggatctt cttgagatcc ttttttttctg    4140 cgcgtaatct gctgcttgca acaaaaaaaa ccaccgctac cagcggtggt ttgtttgccg    4200
gatcaagagc taccaactct ttttccgaag gtaactggct tcagcagagc gcagatacca    4260
aatactgtcc ttctagtgta gccgtagtta ggccaccact tcaagaactc tgtagcaccg    4320
cctacatacc tcgctctgct aatcctgtta ccagtggctg ctgccagtgg cgataagtcg    4380
tgtcttaccg ggttggactc aagacgatag ttaccggata aggcgcagcg gtcgggctga    4440
acggggggtt cgtgcacaca gcccagcttg gagcgaacga cctacaccga actgagatac    4500
ctacagcgtg agctatgaga aagcgccacg cttcccgaag ggagaaaggc ggacaggtat    4560
ccggtaagcg gcagggtcgg aacaggagag cgcacgaggg agcttccagg gggaaacgcc    4620
tggtatcttt atagtcctgt cgggtttcgc cacctctgac ttgagcgtcg atttttgtga    4680
tgctcgtcag ggggcggag cctatggaaa aacgccagca acgcggcctt tttacggttc    4740
ctggcctttt gctggccttt tgctcacatg ttctttcctg cgttatcccc tgattctgtg    4800
gataaccgta ttaccgcctt tgagtgagct gataccgctc gccgcagccg aacgaccgag    4860
cgcagcgagt cagtgagcga ggaagcggaa gagcgcccaa tacgcaaacc gcctctcccc    4920
gcgcgttggc cgattcatta atgcagctgg cacgacaggt ttcccgactg gaaagcgggc    4980
agtgagcgca acgcaattaa tgtgagttag ctcactcatt aggcacccca ggctttacac    5040
tttatgcttc cggctcgtat gttgtgtgga attgtgagcg gataacaatt tcacacagga    5100
aacagctatg accatgatta cg                                              5122
```

<210> SEQ ID NO 3
<211> LENGTH: 4827
<212> TYPE: DNA
<213> ORGANISM: Artificial Sequence
<220> FEATURE:
<223> OTHER INFORMATION: Synthetic oligonucleotide

<400> SEQUENCE: 3

```
ccggtgccac catggcccct ggctcccgga cctccctgct gctggccttc ggcctgctgt      60
gcctgccttg gctgcaggaa ggctccgcct tccctaccat ccctctgtcc cggctgttcg     120
acaacgccat gctgcgggcc caccggctgc accagctggc ctttgacacc taccaggaat     180
ttgaggaagc ctacatccct aaggaacaga agtactcctt cctgcagaac cctcagacca     240
gcctgtgctt ctccgagtcc atccctaccc cttccaaccg ggaggaaaca cagcagaagt     300
ccaacctgga gctgctgcgg atcagcctgc tgctgatcca gtcctggctg agcctgtgc     360 agttcctgcg gtccgtgttc gccaactccc tggtgtacgg cgcctccgac tccaacgtgt     420
acgacctgct gaaggacctg gaggaaggca tccagaccct gatgggcaga ctggaggacg     480
gctcccctcg gaccggccag atcttcaagc agacctactc caagttcgac accaactccc     540
acaacgacga cgccctgctg aagaactatg gcctgctgta ctgcttccgg aaggacatgg     600
acaaggtgga cattcctgc ggatcgtgc agtgccggtc cgtggaggc cctgcggct     660 tctgagatat caatgaatgc aattgttgtt gttaacttgt ttattgcagc ttataatggt     720
tacaaataaa gcaatagcat cacaaatttc acaaataaag cattttttc actgcattct     780 agttgtggtt tgtccaaact catcaatgta tcttatcatg tctgaattcg taatcatggt     840
```

```
catagctgtt tcctgtgtga aattgttatc cgctcacaat tccacacaac atacgagccg    900
gaagcataaa gtgtaaagcc tggggtgcct aatgagtgag ctaactcaca ttaattgcgt    960
tgcgctcact gcccgctttc cagtcgggaa acctgtcgtg ccagctgcat taatgaatcg   1020
gccaacgcgc ggggagaggc ggtttgcgta ttgggcgctc ttccgcttcc tcgctcactg   1080
actcgctgcg ctcggtcgtt cggctgcggc gagcggtatc agctcactca aaggcggtaa   1140
tacggttatc cacagaatca ggggataacg caggaaagaa catgtgagca aaaggccagc   1200
aaaaggccag gaaccgtaaa aaggccgcgt tgctggcgtt tttccatagg ctccgccccc   1260
ctgacgagca tcacaaaaat cgacgctcaa gtcagaggtg cgaaacccg acaggactat    1320 aaagatacca ggcgtttccc cctggaagct ccctcgtgcg ctctcctgtt ccgaccctgc   1380
cgcttaccgg atacctgtcc gcctttctcc cttcgggaag cgtggcgctt tctcatagct   1440
cacgctgtag gtatctcagt tcggtgtagg tcgttcgctc caagctgggc tgtgtgcacg   1500
aaccccccgt tcagcccgac cgctgcgcct tatccggtaa ctatcgtctt gagtccaacc   1560
cggtaagaca cgacttatcg ccactggcag cagccactgg taacaggatt agcagagcga   1620
ggtatgtagg cggtgctaca gagttcttga agtggtggcc taactacggc tacactagaa   1680
ggacagtatt tggtatctgc gctctgctga gccagttac cttcggaaaa agagttggta    1740
gctcttgatc cggcaaacaa accaccgctg gtagcggtgg ttttttgtt tgcaagcagc    1800 agattacgcg cagaaaaaaa ggatctcaag aagatccttt gatcttttct acggggtctg   1860
acgctcagtg gaacgaaaac tcacgttaag gattttggt catgagatta tcaaaaagga    1920
tcttccccta gatccttta aattaaaaat gaagttttaa atcaatctaa agtatatatg    1980
agtaaacttg gtctgacagt taccaatgct taatcagtga ggcacctatc tcagcgatct   2040
gtctatttcg ttcatccata gttgcctgac tccccgtcgt gtagataact acgatacggg   2100
agggcttacc atctggcccc agtgctgcaa tgataccgcg agacccacgc tcaccggctc   2160
cagatttatc agcaataaac cagccagccg aagggccga gcagaagt ggtcctgcaa     2220 ctttatccgc ctccatccag tctattaatt gttgccggga agctagagta agtagttcgc   2280
cagttaatag tttgcgcaac gttgttgcca ttgctacagg catcgtggtg tcacgctcgt   2340
cgtttggtat ggcttcattc agctccggtt cccaacgatc aaggcgagtt acatgatccc   2400
ccatgttgtg caaaaaagcg gttagctcct tcggtcctcc gatcgttgtc agaagtaagt   2460
tggccgcagt gttatcactc atggttatgg cagcactgca taattctctt actgtcatgc   2520
catccgtaag atgcttttct gtgactggtg agtactcaac caagtcattc tgagaatagt   2580
gtatgcggcg accgagttgc tcttgcccgg cgtcaatacg gataataccg cgccacata    2640 gcagaacttt aaaagtgctc atcattggaa aacgttcttc ggggcgaaaa ctctcaagga   2700
tcttaccgct gttgagatcc agttcgatgt aacccactcg tgcacccaac tgatcttcag   2760
catcttttac tttcaccagc gtttctgggt gagcaaaaac aggaaggcaa aatgccgcaa   2820
aaaagggaat aagggcgaca cggaaatgtt gaatactcat actcttcctt tttcaatatt   2880
attgaagcat ttatcagggt tattgtctca tgagcggata catatttgaa tgtatttaga   2940
aaaataaaca ataggggtt ccgcgcacat ttccccgaaa agtgccacct gacgtccaca    3000
caaaaaacca acacacagat gtaatgaaaa taaagatatt ttattgcggc catcgtgatg   3060
gcaggttggg cgtcgcttgg tcggtcattt cgaaccccag agtccgctc agaagaactc    3120 gtcaagaagg cgatagaagg cgatgcgctg cgaatcggga gcggcgatac cgtaaagcac   3180
gaggaagcgg tcagcccatt cgccgccaag ctcttcagca atatcacggg tagccaacgc   3240
```

```
tatgtcctga tagcggtccg ccacacccag ccggccacag tcgatgaatc cagaaaagcg    3300
gccattttcc accatgatat tcggcaagca ggcatcgcca tgggtcacga cgagatcctc    3360
gccgtcgggc atgcgcgcct tgagcctggc gaacagttcg gctggcgcga gccctgatg    3420 ctcttcgtcc agatcatcct gatcgacaag accggcttcc atccgagtac gtgctcgctc    3480
gatgcgatgt ttcgcttggt ggtcgaatgg gcaggtagcc ggatcaagcg tatgcagccg    3540
ccgcattgca tcagccatga tggatacttt ctcggcagga gcaaggtgag atgacaggag    3600
atcctgcccc ggcacttcgc ccaatagcag ccagtccctt cccgcttcag tgacaacgtc    3660
gagcacagct gcgcaaggaa cgcccgtcgt ggccagccac gatagccgcg ctgcctcgtc    3720
ctgcagttca ttcagggcac cggacaggtc ggtcttgaca aaagaaccg gcgcccctg    3780 cgctgacagc cggaacacgg cggcatcaga gcagccgatt gtctgttgtg cccagtcata    3840
gccgaatagc ctctccaccc aagcggccgg agaacctgcg tgcaatccat cttgttcaat    3900
catagctcag aggccgaggc ggcctcggcc tctgcataaa taaaaaaaat tagtcagcca    3960
tggggcggag aatgggcgga actgggcgga gctcagaggc cgaggcggcc tcggcctctg    4020
cataaataaa aaaaattagt cagccatggg gcggagaatg gcggaactg gcgggatc    4080 ctcaatattg gccattagcc atattattca ttggttatat agcataaatc aatattggct    4140
attggccatt gcatacgttg tatctatatc ataatatgta catttatatt ggctcatgtc    4200
caatatgacc gccatgttgg cattgattat tgactagtta ttaatagtaa tcaattacgg    4260
ggtcattagt tcatagccca tatatggagt tccgcgttac ataacttacg gtaaatggcc    4320
cgcctggctg accgcccaac gacccccgcc cattgacgtc aataatgacg tatgttccca    4380
tagtaacgcc aatagggact ttccattgac gtcaatgggt ggagtattta cggtaaactg    4440
cccacttggc agtacatcaa gtgtatcata tgccaagtcc gccccctatt gacgtcaatg    4500
acggtaaatg gcccgcctgg cattatgccc agtacatgac cttacgggac tttcctactt    4560
ggcagtacat ctacgtatta gtcatcgcta ttaccatggt gatgcggttt tggcagtaca    4620
ccaatgggcg tggatagcgg tttgactcac ggggatttcc aagtctccac cccattgacg    4680
tcaatgggag tttgttttgg caccaaaatc aacgggactt tccaaaatgt cgtaataacc    4740
ccgccccgtt gacgcaaatg ggcggtaggc gtgtacggtg ggaggtctat ataagcagag    4800
ctcgtttagt gaaccgtcag atcaaaa                                        4827
```

<210> SEQ ID NO 4
<211> LENGTH: 5026
<212> TYPE: DNA
<213> ORGANISM: Artificial Sequence
<220> FEATURE:
<223> OTHER INFORMATION: Synthetic oligonucleotide

<400> SEQUENCE: 4

```
gacgaaaggg cctcgtgata cgcctatttt tataggttaa tgtcatgata ataatggttt      60
cttagacgtc aggtggcact tttcggggaa atgtgcgcgg aaccccctatt tgtttatttt    120 tctaaataca ttcaaatatg tatccgctca tgagacaata accctgataa atgcttcaat    180
aatattgaaa aaggaagagt atgagtattc aacatttccg tgtcgccctt attcccttttt    240 ttgcggcatt ttgccttcct gtttttgctc acccagaaac gctggtgaaa gtaaaagatg    300
ctgaagatca gttgggtgca cgagtgggtt acatcgaact ggatctcaac agcggtaaga    360
tccttgagag ttttcgcccc gaagaacgtt ttccaatgat gagcactttt aaagttctgc    420
```

```
tatgtggcgc ggtattatcc cgtattgacg ccgggcaaga gcaactcggt cgccgcatac    480
actattctca gaatgacttg gttgagtact caccagtcac agaaaagcat cttacggatg    540
gcatgacagt aagagaatta tgcagtgctg ccataaccat gagtgataac actgcggcca    600
acttacttct gacaacgatc ggaggaccga aggagctaac cgcttttttg cacaacatgg    660
gggatcatgt aactcgcctt gatcgttggg aaccggagct gaatgaagcc ataccaaacg    720
acgagcgtga caccacgatg cctgtagcaa tggcaacaac gttgcgcaaa ctattaactg    780
gcgaactact tactctagct tcccggcaac aattaataga ctggatggag gcggataaag    840
ttgcaggacc acttctgcgc tcggcccttc cggctggctg gtttattgct gataaatctg    900
gagccggtga gcgtgggtct cgcggtatca ttgcagcact ggggccagat ggtaagccct    960
cccgtatcgt agttatctac acgacgggga gtcaggcaac tatggatgaa cgaaatagac   1020
agatcgctga gataggtgcc tcactgatta agcattggta actgtcagac caagtttact   1080
catatatact ttagattgat ttaaaacttc attttttaatt taaaaggatc taggtgaaga   1140
tcctttttga taatctcatg accaaaatcc cttaacgtga gttttcgttc cactgagcgt   1200 cagacccgt agaaaagatc aaaggatctt cttgagatcc ttttttttctg cgcgtaatct   1260 gctgcttgca acaaaaaaa ccaccgctac cagcggtggt ttgtttgccg gatcaagagc   1320
taccaactct ttttccgaag gtaactggct tcagcagagc gcagatacca aatactgtcc   1380
ttctagtgta gccgtagtta ggccaccact tcaagaactc tgtagcaccg cctacatacc   1440
tcgctctgct aatcctgtta ccagtggctg ctgccagtgg cgataagtcg tgtcttaccg   1500
ggttggactc aagacgatag ttaccggata aggcgcagcg tcgggctga acggggggtt   1560 cgtgcacaca gcccagcttg gagcgaacga cctacaccga actgagatac ctacagcgtg   1620
agctatgaga aagcgccacg cttcccgaag ggagaaaggc ggacaggtat ccggtaagcg   1680
gcagggtcgg aacaggagag cgcacgaggg agcttccagg gggaaacgcc tggtatcttt   1740
atagtcctgt cgggtttcgc cacctctgac ttgagcgtcg attttttgtga tgctcgtcag   1800 gggggcggag cctatggaaa aacgccagca acgcggcctt tttacggttc ctggcctttt   1860 gctgccttt tgctcacatg ttctttcctg cgttatcccc tgattctgtg ataaccgta    1920 ttaccgcctt tgagtgagct gataccgctc gccgcagccg aacgaccgag cgcagcgagt   1980
cagtgagcga ggaagcggaa gagcgcccaa tacgcaaacc gcctctcccc gcgcgttggc   2040
cgattcatta atgcagctgg cacgacaggt ttcccgactg gaaagcgggc agtgagcgca   2100
acgcaattaa tgtgagttag ctcactcatt aggcacccca ggctttacac tttatgcttc   2160
cggctcgtat gttgtgtgga attgtgagcg gataacaatt tcacacagga aacagctatg   2220
accatgatta cgaattccag ctgtggaatg tgtgtcagtt agggtgtgga aagtccccag   2280
gctccccagc aggcagaagt atgcaaagca tgcatctcaa ttagtcagca accaggtgtg   2340
gaaagtcccc aggctcccca gcaggcagaa gtatgcaaag catgcatctc aattagtcag   2400
caaccatagt cccgccccta actccgccca tcccgcccct aactccgccc agttccgccc   2460
attctccgcc ccatggctga ctaattttttt ttatttatgc agaggccgag gccgcctcgg   2520
cctctgagct attccagaag tagtgaggag gcttttttgg aggcctaggc ttttgcaaaa   2580
agcgatcctg agaacttcag ggtgagtttg ggacccttga ttgttctttc ttttttcgct   2640
attgtaaaat tcatgttata tggaggggc aaagttttca gggtgttgtt tagaatggga   2700
agatgtccct tgtatcacca tggacccttca tgataattttt gtttcttttca cttttctactc   2760 tgttgacaac cattgtctcc tcttattttc ttttcatttt ctgtaacttt ttcgttaaac   2820
```

```
tttagcttgc atttgtaacg aattttttaaa ttcacttttg tttatttgtc agattgtaag    2880
tactttctct aatcactttt ttttcaaggc aatcagggta tattatattg tacttcagca    2940
cagttttaga gaacaattgt tataattaaa tgataaggta gaatatttct gcatataaat    3000
tctggctggc gtggaaatat tcttattggt agaaacaact acatcctggt catcatcctg    3060
cctttctctt tatggttaca atgatataca ctgtttgaga tgaggataaa atactctgag    3120
tccaaaccgg gcccctctgc taaccatgtt catgccttct tcttttttcct acagctcctg   3180
ggcaacgtgc tggttgttgt gctgtctcat cattttggca aaaccggtta gtgatatcaa    3240
tgaatgcaat tgttgttgtt aacttgttta ttgcagctta taatggttac aaataaagca    3300
atagcatcac aaatttcaca aataaagcat ttttttcact gcattctagt tgtggtttgt    3360
ccaaactcat caatgtatct tatcatgtct ggatcccggg gatcctctag acagctgtgg    3420
aatgtgtgtc agttagggtg tggaaagtcc ccaggctccc cagcaggcag aagtatgcaa    3480
agcatgcatc tcaattagtc agcaaccagg tgtggaaagt ccccaggctc ccagcaggc    3540
agaagtatgc aaagcatgca tctcaattag tcagcaacca tagtcccgcc cctaactccg    3600
cccatcccgc ccctaactcc gcccagttcc gcccattctc cgccccatgg ctgactaatt    3660
tttttttattt atgcagaggc cgaggccgcc tcggcctctg agctattcca gaagtagtga    3720
ggaggctttt ttggaggcct aggcttttgc aaaaagctca tcgatggcaa tcctagcgtg    3780
aaggctggta ggattttatc cccgctgcca tcatggttcg accattgaac tgcatcgtcg    3840
ccgtgtccca aaatatgggg attggcaaga acggagacct accctggcct ccgctcagga    3900
acgagttcaa gtacttccaa agaatgacca caacctcttc agtggaaggt aaacagaatc    3960
tggtgattat gggtaggaaa acctggttct ccattcctga gaagaatcga cctttaaagg    4020
acagaattaa tatagttctc agtagagaac tcaaagaacc accacgagga gctcattttc    4080
ttgccaaaag tttggatgat gccttaagac ttattgaaca accggaattg gcaagtaaag    4140
tagacatggt ttgatagtc ggaggcagtt ctgtttacca ggaagccatg aatcaaccag    4200
gccacctcag actctttgtg acaaggatca tgcaggaatt tgaaagtgac acgttttttcc    4260
cagaaattga tttggggaaa tataaacttc tcccagaata cccaggcgtc ctctctgagg    4320
tccaggagga aaaaggcatc aagtataagt ttgaagtcta cgagaagaaa gactaacagg    4380
aagatgcttt caagttctct gctcccctcc taaagctatg catttttata agaccatggg    4440
acttttgctg gctttagatc ctcgagaatg aatgcaattg ttgttgttaa cttgtttatt    4500
gcagcttata atggttacaa ataaagcaat agcatcacaa atttcacaaa taaagcattt    4560
ttttcactgc attctagttg tggtttgtcc aaactcatca atgtatctta tcatgtctgg    4620
ataagcttgg cactggccgt cgttttacaa cgtcgtgact gggaaaaccc tggcgttacc    4680
caacttaatc gccttgcagc acatccccct ttcgccagct ggcgtaatag cgaagaggcc    4740
cgcaccgatc gcccttccca acagttgcgc agcctgaatg gcgaatggcg cctgatgcgg    4800
tattttctcc ttacgcatct gtgcggtatt tcacaccgca tatggtgcac tctcagtaca    4860
atctgctctg atgccgcata gttaagccag ccccgacacc cgccaacacc cgctgacgcg    4920
ccctgacggg cttgtctgct cccggcatcc gcttacagac aagctgtgac cgtctccggg    4980
agctgcatgt gtcagaggtt ttcaccgtca tcaccgaaac gcgcga              5026
```

<210> SEQ ID NO 5
<211> LENGTH: 5133
<212> TYPE: DNA

<213> ORGANISM: Artificial Sequence
<220> FEATURE:
<223> OTHER INFORMATION: Synthetic oligonucleotide

<400> SEQUENCE: 5

```
cgatggcaat cctagcgtga aggctggtag gattttatcc ccgctgccat catggttcga      60
ccattgaact gcatcgtcgc cgtgtcccaa aatatgggga ttggcaagaa cggagaccta     120
ccctggcctc cgctcaggaa cgagttcaag tacttccaaa gaatgaccac aacctcttca     180
gtggaaggta aacagaatct ggtgattatg ggtaggaaaa cctggttctc cattcctgag     240
aagaatcgac ctttaaagga cagaattaat atagttctca gtagagaact caaagaacca     300
ccacgaggag ctcattttct tgccaaaagt ttggatgatg ccttaagact tattgaacaa     360
ccggaattgg caagtaaagt agacatggtt tggatagtcg gaggcagttc tgtttaccag     420
gaagccatga atcaaccagg ccacctcaga ctctttgtga caaggatcat gcaggaattt     480
gaaagtgaca cgttttttccc agaaattgat ttggggaaat ataaacttct cccagaatac     540
ccaggcgtcc tctctgaggt ccaggaggaa aaaggcatca agtataagtt tgaagtctac     600
gagaagaaag actaacagga agatgctttc aagttctctg ctcccctcct aaagctatgc     660
atttttataa gaccatggga cttttgctgg ctttagatcc tcgagaatga atgcaattgt     720
tgttgttaac ttgtttattg cagcttataa tggttacaaa taaagcaata gcatcacaaa     780
tttcacaaat aaagcatttt tttcactgca ttctagttgt ggtttgtcca aactcatcaa     840
tgtatcttat catgtctgga taagcttggc actggccgtc gttttacaac gtcgtgactg     900
ggaaaaccct ggcgttaccc aacttaatcg ccttgcagca catccccctt tcgccagctg     960
gcgtaatagc gaagaggccc gcaccgatcg cccttcccaa cagttgcgca gcctgaatgg    1020
cgaatggcgc ctgatgcggt attttctcct tacgcatctg tgcggtattt cacaccgcat    1080
atggtgcact ctcagtacaa tctgctctga tgccgcatag ttaagccagc cccgacaccc    1140
gccaacaccc gctgacgcgc cctgacgggc ttgtctgctc ccggcatccg cttacagaca    1200
agctgtgacc gtctccggga gctgcatgtg tcagaggttt tcaccgtcat caccgaaacg    1260
cgcgagacga aagggcctcg tgatacgcct atttttatag gttaatgtca tgataataat    1320
ggtttcttag acgtcaggtg gcacttttcg gggaaatgtg cgcggaaccc ctatttgttt    1380
atttttctaa atacattcaa atatgtatcc gctcatgaga caataaccct gataaatgct    1440
tcaataatat tgaaaaagga agagtatgag tattcaacat ttccgtgtcg cccttattcc    1500
cttttttgcg gcattttgcc ttcctgtttt tgctcaccca gaaacgctgg tgaaagtaaa    1560
agatgctgaa gatcagttgg gtgcacgagt gggttacatc gaactggatc tcaacagcgg    1620
taagatcctt gagagttttc gccccgaaga acgttttcca atgatgagca cttttaaagt    1680
tctgctatgt ggcgcggtat tatcccgtat tgacgccggg caagagcaac tcggtcgccg    1740
catacactat tctcagaatg acttggttga gtactcacca gtcacagaaa agcatcttac    1800
ggatggcatg acagtaagag aattatgcag tgctgccata accatgagtg ataacactgc    1860
ggccaactta cttctgacaa cgatcggagg accgaaggag ctaaccgctt ttttgcacaa    1920
catgggggat catgtaactc gccttgatcg ttgggaaccg gagctgaatg aagccatacc    1980
aaacgacgag cgtgacacca cgatgcctgt agcaatggca acaacgttgc gcaaactatt    2040
aactggcgaa ctacttactc tagcttcccg gcaacaatta atagactgga tggaggcgga    2100
taaagttgca ggaccacttc tgcgctcggc ccttccggct ggctggttta ttgctgataa    2160
atctggagcc ggtgagcgtg ggtctcgcgg tatcattgca gcactggggc cagatggtaa    2220
```

```
gccctcccgt atcgtagtta tctacacgac ggggagtcag gcaactatgg atgaacgaaa    2280
tagacagatc gctgagatag gtgcctcact gattaagcat tggtaactgt cagaccaagt    2340
ttactcatat atactttaga ttgatttaaa acttcatttt taatttaaaa ggatctaggt    2400
gaagatcctt tttgataatc tcatgaccaa atcccttaa cgtgagtttt cgttccactg     2460
agcgtcagac cccgtagaaa agatcaaagg atcttcttga gatccttttt ttctgcgcgt    2520
aatctgctgc ttgcaaacaa aaaaccacc gctaccagcg gtggtttgtt tgccggatca     2580
agagctacca actcttttc cgaaggtaac tggcttcagc agagcgcaga taccaaatac     2640
tgtccttcta gtgtagccgt agttaggcca ccacttcaag aactctgtag caccgcctac    2700
atacctcgct ctgctaatcc tgttaccagt ggctgctgcc agtggcgata agtcgtgtct    2760
taccgggttg gactcaagac gatagttacc ggataaggcg cagcggtcgg gctgaacggg    2820
gggttcgtgc acacagccca gcttggagcg aacgacctac accgaactga gatacctaca    2880
gcgtgagcta tgagaaagcg ccacgcttcc cgaagggaga aaggcggaca ggtatccggt    2940
aagcggcagg gtcggaacag gagagcgcac gagggagctt ccaggggaa acgcctggta     3000 tctttatagt cctgtcgggt ttcgccacct ctgacttgag cgtcgatttt tgtgatgctc    3060 gtcaggggg cggagcctat ggaaaaacgc cagcaacgcg gccttttac ggttcctggc      3120 cttttgctgg ccttttgctc acatgttctt cctgcgtta tccctgatt ctgtggataa      3180 ccgtattacc gcctttgagt gagctgatac cgctcgccgc agccgaacga ccgagcgcag    3240
cgagtcagtg agcgaggaag cggaagagcg cccaatacgc aaaccgcctc tccccgcgcg    3300
ttggccgatt cattaatgca gctggcacga caggtttccc gactggaaag cgggcagtga    3360
gcgcaacgca attaatgtga gttagctcac tcattaggca ccccaggctt tacactttat    3420
gcttccggct cgtatgttgt gtggaattgt gagcggataa caatttcaca caggaaacag    3480
ctatgaccat gattacggat cccgggcgca gcaccatggc ctgaaataac ctctgaaaga    3540
ggaacttggt taggtacctt ctgaggcgga agaaccagc tgtggaatgt gtgtcagtta     3600
gggtgtggaa agtccccagg ctcccccagca ggcagaagta tgcaaagcat gcatctcaat    3660
tagtcagcaa ccaggtgtgg aaagtcccca ggctccccag caggcagaag tatgcaaagc    3720
atgcatctca attagtcagc aaccatagtc ccgcccctaa ctccgcccat cccgcccta     3780 actccgccca gttccgccca ttctccgccc catggctgac taattttttt tatttatgca    3840
gaggccgagg ccgcctcggc ctctgagcta ttccagaagt agtgaggagg ctttttgga    3900 ggcctaggct tttgcaaaaa gctgatcctg agaacttcag ggtgagtttg ggacccttg     3960 attgttcttt cttttcgct attgtaaaat tcatgttata tggagggggc aaagttttca    4020
gggtgttgtt tagaatggga agatgtccct tgtatcacca tggaccctca tgataatttt    4080
gtttctttca ctttctactc tgttgacaac cattgtctcc tcttatttc ttttcatttt    4140 ctgtaacttt tcgttaaac tttagcttgc atttgtaacg aatttttaaa ttcacttttg    4200
tttatttgtc agattgtaag tactttctct aatcactttt ttttcaaggc aatcagggta    4260
tattatattg tacttcagca cagttttaga gaacaattgt tataattaaa tgataaggta    4320
gaatatttct gcatataaat tctggctggc gtggaaatat tcttattggt agaaacaact    4380
acatcctggt catcatcctg cctttctctt tatggttaca atgatataca ctgtttgaga    4440
tgaggataaa atactctgag tccaaaccgg gcccctctgc taaccatgtt catgccttct    4500
tctttttcct acagctcctg ggcaacgtgc tggttgttgt gctgtctcat catttggca    4560
```

| | |
|---|---|
| aagtcgacga cgaacgcgtt aacgttactg gccgaagccg cttggaataa ggccggtgtg | 4620 |
| cgtttgtcta tatgtgattt tccaccatat tgccgtcttt tggcaatgtg agggcccgga | 4680 |
| aacctggccc tgtcttcttg acgagcattc ctaggggtct ttcccctctc gccaaaggaa | 4740 |
| tgcaaggtct gttgaatgtc gtgaaggaag cagttcctct ggaagcttct tgaagacaaa | 4800 |
| caacgtctgt agcgacccct tgcaggcagc ggaaccccc acctggcgac aggtgcctct | 4860 |
| gcggccaaaa gccacgtgta taagatacac ctgcaaaggc ggcacaaccc cagtgccacg | 4920 |
| ttgtgagttg atagttgtg gaaagagtca aatggctctc ctcaagcgta ttcaacaagg | 4980 |
| ggctgaagga tgcccagaag gtaccccatt gtatgggatc tgatctgggg cctcggtgca | 5040 |
| catgctttac atgtgtttag tcgaggttaa aaaaacgtct aggcccccg aaccacgggg | 5100 |
| acgtggtttt cctttgaaaa acacgatgat aat | 5133 |

<210> SEQ ID NO 6
<211> LENGTH: 6250
<212> TYPE: DNA
<213> ORGANISM: Artificial Sequence
<220> FEATURE:
<223> OTHER INFORMATION: Synthetic oligonucleotide

<400> SEQUENCE: 6

| | |
|---|---|
| gacgaaaggg cctcgtgata cgcctatttt tataggttaa tgtcatgata ataatggttt | 60 |
| cttagacgtc aggtggcact tttcggggaa atgtgcgcgg aacccctatt tgtttatttt | 120 |
| tctaaataca ttcaaatatg tatccgctca tgagacaata accctgataa atgcttcaat | 180 |
| aatattgaaa aaggaagagt atgagtattc aacatttccg tgtcgccctt attccctttt | 240 |
| ttgcggcatt ttgccttcct gttttttgctc acccagaaac gctggtgaaa gtaaaagatg | 300 |
| ctgaagatca gttgggtgca cgagtgggtt acatcgaact ggatctcaac agcggtaaga | 360 |
| tccttgagag ttttcgcccc gaagaacgtt ttccaatgat gagcactttt aaagttctgc | 420 |
| tatgtggcgc ggtattatcc cgtattgacg ccgggcaaga gcaactcggt cgccgcatac | 480 |
| actattctca gaatgacttg gttgagtact caccagtcac agaaaagcat cttacggatg | 540 |
| gcatgacagt aagagaatta tgcagtgctg ccataaccat gagtgataac actgcggcca | 600 |
| acttacttct gacaacgatc ggaggaccga aggagctaac cgcttttttg cacaacatgg | 660 |
| gggatcatgt aactcgcctt gatcgttggg aaccggagct gaatgaagcc ataccaaacg | 720 |
| acgagcgtga caccacgatg cctgtagcaa tggcaacaac gttgcgcaaa ctattaactg | 780 |
| gcgaactact tactctagct tcccggcaac aattaataga ctggatggag gcggataaag | 840 |
| ttgcaggacc acttctgcgc tcggcccttc cggctggctg gtttattgct gataaatctg | 900 |
| gagccggtga gcgtgggtct cgcggtatca ttgcagcact ggggccagat ggtaagccct | 960 |
| cccgtatcgt agttatctac acgacgggga gtcaggcaac tatggatgaa cgaaatagac | 1020 |
| agatcgctga gataggtgcc tcactgatta agcattggta actgtcagac caagtttact | 1080 |
| catatatact ttagattgat ttaaaacttc attttttaatt taaaaggatc taggtgaaga | 1140 |
| tccttttga taatctcatg accaaaatcc cttaacgtga gttttcgttc cactgagcgt | 1200 |
| cagacccgt agaaaagatc aaaggatctt cttgagatcc tttttttctg cgcgtaatct | 1260 |
| gctgcttgca acaaaaaaa ccaccgctac cagcggtggt ttgtttgccg gatcaagagc | 1320 |
| taccaactct ttttccgaag gtaactggct tcagcagagc gcagatacca atactgtcc | 1380 |
| ttctagtgta gccgtagtta ggccaccact tcaagaactc tgtagcaccg cctacatacc | 1440 |
| tcgctctgct aatcctgtta ccagtggctg ctgccagtgg cgataagtcg tgtcttaccg | 1500 |

```
ggttggactc aagacgatag ttaccggata aggcgcagcg gtcgggctga acgggggggtt   1560 cgtgcacaca gcccagcttg gagcgaacga cctacaccga actgagatac ctacagcgtg   1620
agctatgaga aagcgccacg cttcccgaag ggagaaaggc ggacaggtat ccggtaagcg   1680
gcagggtcgg aacaggagag cgcacgaggg agcttccagg gggaaacgcc tggtatcttt   1740
atagtcctgt cgggtttcgc cacctctgac ttgagcgtcg attttttgtga tgctcgtcag   1800 gggggcggag cctatggaaa aacgccagca acgcggcctt tttacggttc ctggccttttt   1860 gctggccttt tgctcacatg ttcttttcctg cgttatcccc tgattctgtg gataaccgta   1920
ttaccgcctt tgagtgagct gataccgctc gccgcagccg aacgaccgag cgcagcgagt   1980
cagtgagcga ggaagcggaa gagcgcccaa tacgcaaacc gcctctcccc gcgcgttggc   2040
cgattcatta atgcagctgg cacgacaggt ttcccgactg gaaagcgggc agtgagcgca   2100
acgcaattaa tgtgagttag ctcactcatt aggcacccca ggctttacac tttatgcttc   2160
cggctcgtat gttgtgtgga attgtgagcg gataacaatt tcacacagga aacagctatg   2220
accatgatta cgaattccag ctgtggaatg tgtgtcagtt agggtgtgga agtccccag    2280 gctccccagc aggcagaagt atgcaaagca tgcatctcaa ttagtcagca accaggtgtg   2340
gaaagtcccc aggctcccca gcaggcagaa gtatgcaaag catgcatctc aattagtcag   2400
caaccatagt cccgccccta actccgccca tcccgcccct aactccgccc agttccgccc   2460
attctccgcc ccatggctga ctaatttttt ttatttatgc agaggccgag gccgcctcgg   2520
cctctgagct attccagaag tagtgaggag gcttttttgg aggcctaggc ttttgcaaaa   2580
agcgatcctg agaacttcag ggtgagtttg ggacccttg attgttcttt cttttttcgct   2640 attgtaaaat tcatgttata tggagggggc aaagttttca gggtgttgtt tagaatggga   2700
agatgtccct tgtatcacca tggaccctca tgataatttt gtttctttca cttttctactc   2760 tgttgacaac cattgtctcc tcttattttc ttttcatttt ctgtaacttt tcgttaaac    2820 tttagcttgc atttgtaacg aatttttaaa ttcacttttg tttatttgtc agattgtaag   2880
tactttctct aatcactttt ttttcaaggc aatcagggta tattatattg tacttcagca   2940 cagtttttaga gaacaattgt tataattaaa tgataaggta gaatatttct gcatataaat  3000
tctggctggc gtggaaatat tcttattggt agaaacaact acatcctggt catcatcctg   3060
cctttctctt tatggttaca atgatataca ctgtttgaga tgaggataaa atactctgag   3120
tccaaaccgg gcccctctgc taaccatgtt catgccttct tcttttttcct acagctcctg   3180 ggcaacgtgc tggttgttgt gctgtctcat cattttggca aaaccggtta gtgatatcaa   3240
tgaatgcaat tgttgttgtt aacttgttta ttgcagctta taatggttac aaataaagca   3300
atagcatcac aaatttcaca aataaagcat ttttttcact gcattctagt tgtggtttgt   3360
ccaaactcat caatgtatct tatcatgtct ggatcccggg cgcagcacca tggcctgaaa   3420
taacctctga agaggaact tggttaggta ccttctgagg cggaaagaac cagctgtgga   3480
atgtgtgtca gttagggtgt ggaaagtccc caggctcccc agcaggcaga gtatgcaaa    3540 gcatgcatct caattagtca gcaaccaggt gtggaaagtc cccaggctcc ccagcaggca   3600
gaagtatgca aagcatgcat ctcaattagt cagcaaccat agtcccgccc ctaactccgc   3660
ccatcccgcc cctaactccg cccagttccg cccattctcc gccccatggc tgactaattt   3720 ttttttattta tgcagaggcc gaggccgcct cggcctctga gctattccag aagtagtgag   3780
gaggcttttt tggaggccta ggcttttgca aaaagctgat cctgagaact tcagggtgag   3840
```

```
tttggggacc cttgattgtt cttctttttt cgctattgta aaattcatgt tatatggagg       3900
gggcaaagtt ttcagggtgt tgtttagaat gggaagatgt cccttgtatc accatggacc       3960
ctcatgataa ttttgtttct ttcactttct actctgttga caaccattgt ctcctcttat       4020
tttcttttca ttttctgtaa cttttttcgtt aaactttagc ttgcatttgt aacgaattt       4080 taaattcact tttgtttatt tgtcagattg taagtacttt ctctaatcac ttttttttca       4140
aggcaatcag ggtatattat attgtacttc agcacagttt tagagaacaa ttgttataat       4200
taaatgataa ggtagaatat ttctgcatat aaattctggc tggcgtggaa atattcttat       4260
tggtagaaac aactcatcc tggtcatcat cctgcctttc tctttatggt tacaatgata        4320
tacactgttt gagatgagga taaaatactc tgagtccaaa ccgggcccct ctgctaacca      4380
tgttcatgcc ttcttctttt tcctacagct cctgggcaac gtgctggttg ttgtgctgtc      4440
tcatcatttt ggcaaagtcg acgacgaacg cgtaatgaat gcaattgttg ttgttaactt      4500
gtttattgca gctataatg gttacaaata aagcaatagc atcacaaatt tcacaaataa       4560 agcattttt tcactgcatt ctagttgtgg tttgtccaaa ctcatcaatg tatcttatca       4620
tgtctggatt ctagacagct gtggaatgtg tgtcagttag ggtgtggaaa gtccccaggc      4680
tccccagcag gcagaagtat gcaaagcatg catctcaatt agtcagcaac caggtgtgga      4740
aagtccccag gctccccagc aggcagaagt atgcaaagca tgcatctcaa ttagtcagca      4800
accatagtcc cgcccctaac tccgcccatc ccgcccctaa ctccgcccag ttccgcccat      4860
tctccgcccc atggctgact aattttttt atttatgcag aggccgaggc cgcctcggcc       4920
tctgagctat tccagaagta gtgaggaggc ttttttggag gcctaggctt ttgcaaaaag      4980
ctcatcgatg gcaatcctag cgtgaaggct ggtaggattt tatccccgct gccatcatgg      5040
ttcgaccatt gaactgcatc gtcgccgtgt cccaaaatat ggggattggc aagaacggag      5100
acctaccctg gcctccgctc aggaacgagt tcaagtactt ccaaagaatg accacaacct      5160
cttcagtgga aggtaaacag aatctggtga ttatgggtag gaaaacctgg ttctccattc      5220
ctgagaagaa tcgaccttta aaggacagaa ttaatatagt tctcagtaga gaactcaaag      5280
aaccaccacg aggagctcat tttcttgcca aaagtttgga tgatgcctta agacttattg      5340
aacaaccgga attggcaagt aaagtagaca tggtttggat agtcggaggc agttctgttt      5400
accaggaagc catgaatcaa ccaggccacc tcagactctt tgtgacaagg atcatgcagg      5460
aatttgaaag tgacacgttt ttcccagaaa ttgatttggg gaaatataaa cttctcccag      5520
aatacccagg cgtcctctct gaggtccagg aggaaaaagg catcaagtat aagtttgaag      5580
tctacgagaa gaaagactaa caggaagatg ctttcaagtt ctctgctccc ctcctaaagc      5640
tatgcatttt tataagacca tgggactttt gctggcttta gatcctcgag aatgaatgca      5700
attgttgttg ttaacttgtt tattgcagct tataatggtt acaaataaag caatagcatc      5760
acaaatttca caaataaagc attttttca ctgcattcta gttgtggttt gtccaaactc      5820
atcaatgtat cttatcatgt ctggataagc ttggcactgg ccgtcgtttt acaacgtcgt      5880
gactgggaaa accctggcgt tacccaactt aatcgccttg cagcacatcc cctttcgcc       5940 agctggcgta atagcgaaga ggcccgcacc gatcgccctt cccaacagtt gcgcagcctg      6000
aatggcgaat ggcgcctgat gcggtatttt ctccttacgc atctgtgcgg tatttcacac      6060
cgcatatggt gcactctcag tacaatctgc tctgatgccg catagttaag ccagccccga      6120
cacccgccaa cacccgctga cgcgccctga cgggcttgtc tgctcccggc atccgcttac      6180
agacaagctg tgaccgtctc cgggagctgc atgtgtcaga ggttttcacc gtcatcaccg      6240
```

```
                                                                aaacgcgcga                                                        6250

<210> SEQ ID NO 7
<211> LENGTH: 6064
<212> TYPE: DNA
<213> ORGANISM: Artificial Sequence
<220> FEATURE:
<223> OTHER INFORMATION: Synthetic oligonucleotide

<400> SEQUENCE: 7
gatcccgggc gcagcaccat ggcctgaaat aacctctgaa agaggaactt ggttaggtac     60
cttctgaggc ggaaagaacc agctgtggaa tgtgtgtcag ttagggtgtg aaagtcccc    120
aggctcccca gcaggcagaa gtatgcaaag catgcatctc aattagtcag caaccaggtg    180
tggaaagtcc ccaggctccc cagcaggcag aagtatgcaa agcatgcatc tcaattagtc    240
agcaaccata gtcccgcccc taactccgcc catcccgccc ctaactccgc ccagttccgc    300
ccattctccg ccccatggct gactaatttt ttttatttat gcagaggccg aggccgcctc    360
ggcctctgag ctattccaga gtagtgagg aggcttttt ggaggcctag gcttttgcaa    420
aaagctgatc ctgagaactt cagggtgagt ttggggaccc ttgattgttc tttcttttc    480
gctattgtaa aattcatgtt atatggaggg ggcaaagttt cagggtgtt gtttagaatg    540
ggaagatgtc ccttgtatca ccatggaccc tcatgataat tttgtttctt tcactttcta    600
ctctgttgac aaccattgtc tcctcttatt ttctttcat tttctgtaac ttttcgtta    660
aactttagct tgcatttgta acgaattttt aaattcactt ttgtttattt gtcagattgt    720
aagtactttc tctaatcact ttttttcaa ggcaatcagg gtatattata ttgtacttca    780
gcacagtttt agagaacaat tgttataatt aaatgataag gtagaatatt tctgcatata    840
aattctggct ggcgtggaaa tattcttatt ggtagaaaca actacatcct ggtcatcatc    900
ctgcctttct ctttatggtt acaatgatat acactgtttg agatgaggat aaaatactct    960
gagtccaaac cgggcccctc tgctaaccat gttcatgcct tcttcttttt cctacagctc   1020
ctgggcaacg tgctggttgt tgtgctgtct catcattttg gcaaagtcga cgacgaacgc   1080
gttaacgtta ctggccgaag ccgcttggaa taaggccggt gtgcgtttgt ctatatgtga   1140
ttttccacca tattgccgtc ttttggcaat gtgagggccc ggaaacctgg ccctgtcttc   1200
ttgacgagca ttcctagggg tctttcccct ctcgccaaag gaatgcaagg tctgttgaat   1260
gtcgtgaagg aagcagttcc tctggaagct tcttgaagac aaacaacgtc tgtagcgacc   1320
cttttgcagg agcggaaccc cccacctggc gacaggtgcc tctgcggcca aaagccacgt   1380
gtataagata cacctgcaaa ggcggcacaa ccccagtgcc acgttgtgag ttggatagtt   1440
gtggaaagag tcaaatggct ctcctcaagc gtattcaaca aggggctgaa ggatgcccag   1500
aaggtacccc attgtatggg atctgatctg ggcctcggt gcacatgctt tacatgtgtt   1560
tagtcgaggt taaaaaaacg tctaggcccc ccgaaccacg gggacgtggt ttcctttga    1620
aaaacacgat gataatcgat ggcaatccta gcgtgaaggc tggtaggatt ttatccccgc   1680
tgccatcatg gttcgaccat tgaactgcat cgtcgccgtg tcccaaaata tggggattgg   1740
caagaacgga gacctaccct ggcctccgct caggaacgag ttcaagtact ccaaagaat    1800
gaccacaacc tcttcagtgg aaggtaaaca gaatctggtg attatgggta ggaaacctg    1860
gttctccatt cctgagaaga tcgacctt  aaaggacaga attaatatag ttctcagtag   1920
agaactcaaa gaaccaccac gaggagctca ttttcttgcc aaaagtttgg atgatgcctt   1980
```

```
aagacttatt gaacaaccgg aattggcaag taaagtagac atggtttgga tagtcggagg      2040
cagttctgtt taccaggaag ccatgaatca accaggccac ctcagactct tgtgacaag       2100 gatcatgcag gaatttgaaa gtgacacgtt tttcccagaa attgatttgg ggaaatataa      2160
acttctccca gaatacccag gcgtcctctc tgaggtccag gaggaaaaag gcatcaagta      2220
taagtttgaa gtctacgaga agaaagacta acaggaagat gctttcaagt tctctgctcc      2280
cctcctaaag ctatgcattt ttataagacc atgggacttt tgctggcttt agatcctcga      2340
gaatgaatgc aattgttgtt gttaacttgt ttattgcagc ttataatggt tacaaataaa      2400
gcaatagcat cacaaatttc acaaataaag catttttttc actgcattct agttgtggtt      2460
tgtccaaact catcaatgta tcttatcatg tctggataag cttggcactg gccgtcgttt      2520
tacaacgtcg tgactgggaa accctggcg ttacccaact taatcgcctt gcagcacatc       2580 ccccctttcgc cagctggcgt aatagcgaag aggcccgcac cgatcgccct tcccaacagt    2640
tgcgcagcct gaatggcgaa tggcgcctga tgcggtattt tctccttacg catctgtgcg     2700
gtatttcaca ccgcatatgg tgcactctca gtacaatctg ctctgatgcc gcatagttaa     2760
gccagccccg acacccgcca cacccgctg acgcgccctg acgggcttgt ctgctcccgg      2820
catccgctta cagacaagct gtgaccgtct ccgggagctg catgtgtcag aggttttcac    2880
cgtcatcacc gaaacgcgcg agacgaaagg gcctcgtgat acgcctattt ttataggtta    2940
atgtcatgat aataatggtt tcttagacgt caggtggcac ttttcgggga atgtgcgcg     3000 gaacccctat ttgtttattt ttctaaatac attcaaatat gtatccgctc atgagacaat    3060
aaccctgata aatgcttcaa taatattgaa aaaggaagag tatgagtatt caacatttcc    3120
gtgtcgccct tattccctt tttgcggcat tttgccttcc tgttttgct cacccagaaa      3180 cgctggtgaa agtaaaagat gctgaagatc agttgggtgc acgagtgggt tacatcgaac    3240
tggatctcaa cagcggtaag atccttgaga gttttcgccc cgaagaacgt tttccaatga    3300
tgagcacttt taaagttctg ctatgtggcg cggtattatc ccgtattgac gccgggcaag    3360
agcaactcgg tcgccgcata cactattctc agaatgactt ggttgagtac tcaccagtca    3420
cagaaaagca tcttacggat ggcatgacag taagagaatt atgcagtgct gccataacca    3480
tgagtgataa cactgcggcc aacttacttc tgacaacgat cggaggaccg aaggagctaa    3540 ccgcttttt gcacaacatg ggggatcatg taactcgcct tgatcgttgg aaccggagc      3600 tgaatgaagc cataccaaac gacgagcgtg acaccacgat gcctgtagca atggcaacaa    3660
cgttgcgcaa actattaact ggcgaactac ttactctagc ttcccggcaa caattaatag    3720
actggatgga ggcggataaa gttgcaggac cacttctgcg ctcggccctt ccggctggct    3780
ggtttattgc tgataaatct ggagccggtg agcgtgggtc tcgcggtatc attgcagcac    3840
tggggccaga tggtaagccc tcccgtatcg tagttatcta cacgacgggg agtcaggcaa    3900
ctatggatga acgaaataga cagatcgctg agataggtgc ctcactgatt aagcattggt    3960
aactgtcaga ccaagtttac tcatatatac tttagattga tttaaaactt cattttaat   4020 ttaaaaggat ctaggtgaag atccttttg ataatctcat gaccaaaatc ccttaacgtg      4080
agttttcgtt ccactgagcg tcagacccg tagaaaagat caaaggatct tcttgagatc     4140 cttttttct gcgcgtaatc tgctgcttgc aaacaaaaaa accaccgcta ccagcggtgg     4200
tttgtttgcc ggatcaagag ctaccaactc ttttccgaa ggtaactggc ttcagcagag     4260
cgcagatacc aaatactgtc cttctagtgt agccgtagt aggccaccac ttcaagaact     4320
ctgtagcacc gcctacatac ctcgctctgc taatcctgtt accagtggct gctgccagtg    4380
```

-continued

```
gcgataagtc gtgtcttacc gggttggact caagacgata gttaccggat aaggcgcagc    4440
ggtcgggctg aacgggggt tcgtgcacac agcccagctt ggagcgaacg acctacaccg     4500
aactgagata cctacagcgt gagctatgag aaagcgccac gcttcccgaa gggagaaagg    4560
cggacaggta tccggtaagc ggcagggtcg aacaggaga gcgcacgagg gagcttccag     4620
ggggaaacgc ctggtatctt tatagtcctg tcgggtttcg ccacctctga cttgagcgtc    4680 gattttgtg atgctcgtca gggggcgga gcctatggaa aaacgccagc aacgcggcct     4740
ttttacggtt cctggccttt tgctggcctt ttgctcacat gttctttcct gcgttatccc    4800
ctgattctgt ggataaccgt attaccgcct ttgagtgagc tgataccgct cgccgcagcc    4860
gaacgaccga gcgcagcgag tcagtgagcg aggaagcgga agagcgccca atacgcaaac    4920
cgcctctccc cgcgcgttgg ccgattcatt aatgcagctg gcacgacagg tttcccgact    4980
ggaaagcggg cagtgagcgc aacgcaatta atgtgagtta gctcactcat taggcacccc    5040
aggctttaca ctttatgctt ccggctcgta tgttgtgtgg aattgtgagc ggataacaat    5100
ttcacacagg aaacagctat gaccatgatt acgaattcag acatgataag atacattgat    5160
gagtttggac aaaccacaac tagaatgcag tgaaaaaaat gctttatttg tgaaatttgt    5220
gatgctattg ctttatttgt aaccattata agctgcaata aacaagttaa caacaacaat    5280
tgcattcatt gatatcggtg ctagttaact agaccggttt tgatctgacg gttcactaaa    5340
cgagctctgc ttatatagac ctcccaccgt acacgcctac cgcccatttg cgtcaacggg    5400
gcggggttat tacgacattt tggaaagtcc cgttgatttt ggtgccaaaa caaactccca    5460
ttgacgtcaa tggggtggag acttggaaat ccccgtgagt caaaccgcta ccacgcccca    5520
ttggtgtact gccaaaaccg catcaccatg gtaatagcga tgactaatac gtagatgtac    5580
tgccaagtag gaaagtcccg taaggtcatg tactgggcat aatgccaggc gggccattta    5640
ccgtcattga cgtcaatagg gggcggactt ggcatatgat acacttgatg tactgccaag    5700
tgggcagttt accgtaaata ctccacccat tgacgtcaat ggaaagtccc tattggcgtt    5760
actatgggaa catacgtcat tattgacgtc aatgggcggg ggtcgttggg cggtcagcca    5820
ggcgggccat ttaccgtaag ttatgtaacg cggaactcca tatatgggct atgaactaat    5880
gaccccgtaa ttgattacta ttaataacta gtcaataatc aatgccaaca tggcggtcat    5940
attggacatg agccaatata aatgtacata ttatgatata gatacaacgt atgcaatggc    6000
caatagccaa tattgattta tgctatataa ccaatgaata atatggctaa tggccaatat    6060
tgag                                                                 6064
```

<210> SEQ ID NO 8
<211> LENGTH: 6292
<212> TYPE: DNA
<213> ORGANISM: Artificial Sequence
<220> FEATURE:
<223> OTHER INFORMATION: Synthetic oligonucleotide

<400> SEQUENCE: 8

```
cgatggcaat cctagcgtga aggctggtag gattttatcc ccgctgccat catggttcga     60
ccattgaact gcatcgtcgc cgtgtcccaa aatatgggga ttggcaagaa cggagaccta    120
ccctggcctc cgctcaggaa cgagttcaag tacttccaaa gaatgaccac aacctcttca    180
gtggaaggta aacagaatct ggtgattatg ggtaggaaaa cctggttctc cattcctgag    240
aagaatcgac cttttaagga cagaattaat atagttctca gtagagaact caagaaccca    300
```

```
ccacgaggag ctcatttcct tgccaaaagt ttggatgatg ccttaagact tattgaacaa    360
ccggaattgg caagtaaagt agacatggtt tggatagtcg gaggcagttc tgtttaccag    420
gaagccatga atcaaccagg ccacctcaga ctctttgtga caaggatcat gcaggaattt    480
gaaagtgaca cgttttccc agaaattgat ttggggaaat ataaacttct cccagaatac    540
ccaggcgtcc tctctgaggt ccaggaggaa aaaggcatca agtataagtt tgaagtctac    600
gagaagaaag actaacagga agatgctttc aagttctctg ctcccctcct aaagctatgc    660 attttttataa gaccatggga cttttgctgg ctttagatcc tcgagaatga atgcaattgt    720
tgttgttaac ttgtttattg cagcttataa tggttacaaa taaagcaata gcatcacaaa    780
tttcacaaat aaagcatttt tttcactgca ttctagttgt ggtttgtcca aactcatcaa    840
tgtatcttat catgtctgga taagcttggc actggccgtc gttttacaac gtcgtgactg    900
ggaaaaccct ggcgttaccc aacttaatcg ccttgcagca catccccctt tcgccagctg    960
gcgtaatagc gaagaggccc gcaccgatcc cccttcccaa cagttgcgca gcctgaatgg   1020
cgaatggcgc ctgatgcggt attttctcct tacgcatctg tgcggtattt cacaccgcat   1080
atggtgcact ctcagtacaa tctgctctga tgccgcatag ttaagccagc ccgacaccc   1140 gccaacaccc gctgacgcgc cctgacgggc ttgtctgctc ccggcatccg cttacagaca   1200
agctgtgacc gtctccggga gctgcatgtg tcagaggttt tcaccgtcat caccgaaacg   1260
cgcgagacga agggcctcg tgatacgcct atttttatag gttaatgtca tgataataat   1320
ggtttcttag acgtcaggtg gcacttttcg gggaaatgtg cgcggaaccc ctatttgttt   1380 attttctaa atacattcaa atatgtatcc gctcatgaga caataaccct gataaatgct   1440
tcaataatat tgaaaaagga agagtatgag tattcaacat ttccgtgtcg cccttattcc   1500
cttttttgcg gcattttgcc ttcctgtttt tgctcaccca gaaacgctgg tgaaagtaaa   1560
agatgctgaa gatcagttgg gtgcacgagt gggttacatc gaactggatc tcaacagcgg   1620
taagatcctt gagagttttc gccccgaaga acgttttcca atgatgagca cttttaaagt   1680
tctgctatgt ggcgcggtat tatcccgtat tgacgccggg caagagcaac tcggtcgccg   1740
catacactat tctcagaatg acttggttga gtactcacca gtcacagaaa agcatcttac   1800
ggatggcatg acagtaagag aattatgcag tgctgccata accatgagtg ataacactgc   1860
ggccaactta cttctgacaa cgatcggagg accgaaggag ctaaccgctt ttttgcacaa   1920
catgggggat catgtaactc gccttgatcg ttgggaaccg gagctgaatg aagccatacc   1980
aaacgacgag cgtgacacca cgatgcctgt agcaatggca acaacgttgc gcaaactatt   2040
aactggcgaa ctacttactc tagcttcccg gcaacaatta atagactgga tggaggcgga   2100
taaagttgca ggaccacttc tgcgctcggc ccttccggct ggctggttta ttgctgataa   2160
atctggagcc ggtgagcgtg ggtctcgcgg tatcattgca gcactggggc cagatggtaa   2220
gccctcccgt atcgtagtta tctacacgac ggggagtcag gcaactatgg atgaacgaaa   2280
tagacagatc gctgagatag gtgcctcact gattaagcat tggtaactgt cagaccaagt   2340
ttactcatat atactttaga ttgatttaaa acttcatttt taatttaaaa ggatctaggt   2400
gaagatcctt tttgataatc tcatgaccaa atcccttaa cgtgagtttt cgttccactg   2460
agcgtcagac cccgtagaaa agatcaaagg atcttcttga gatccttttt ttctgcgcgt   2520
aatctgctgc ttgcaaacaa aaaaaccacc gctaccagcg gtggtttgtt tgccggatca   2580
agagctacca actctttttc cgaaggtaac tggcttcagc agagcgcaga taccaaatac   2640
tgtccttcta gtgtagccgt agttaggcca ccacttcaag aactctgtag caccgcctac   2700
```

```
atacctcgct ctgctaatcc tgttaccagt ggctgctgcc agtggcgata agtcgtgtct    2760
taccgggttg gactcaagac gatagttacc ggataaggcg cagcggtcgg gctgaacggg    2820
gggttcgtgc acacagccca gcttggagcg aacgacctac accgaactga gatacctaca    2880
gcgtgagcta tgagaaagcg ccacgcttcc cgaagggaga aaggcggaca ggtatccggt    2940
aagcggcagg gtcggaacag gagagcgcac gagggagctt ccaggggaa acgcctggta    3000 tctttatagt cctgtcgggt ttcgccacct ctgacttgag cgtcgatttt tgtgatgctc    3060
gtcagggggg cggagcctat ggaaaaacgc cagcaacgcg gcctttttac ggttcctggc    3120
cttttgctgg ccttttgctc acatgttctt cctgcgtta tcccctgatt ctgtggataa    3180
ccgtattacc gcctttgagt gagctgatac cgctcgccgc agccgaacga ccgagcgcag    3240
cgagtcagtg agcgaggaag cggaagagcg cccaatacgc aaaccgcctc tccccgcgcg    3300
ttggccgatt cattaatgca gctggcacga caggtttccc gactggaaag cgggcagtga    3360
gcgcaacgca attaatgtga gttagctcac tcattaggca ccccaggctt tacactttat    3420
gcttccggct cgtatgttgt gtggaattgt gagcggataa caatttcaca caggaaacag    3480
ctatgaccat gattacgaat ccagctgtg aatgtgtgt cagttagggt gtggaaagtc    3540
cccaggctcc ccagcaggca gaagtatgca aagcatgcat ctcaattagt cagcaaccag    3600
gtgtggaaag tccccaggct ccccagcagg cagaagtatg caaagcatgc atctcaatta    3660
gtcagcaacc atagtcccgc ccctaactcc gcccatcccg cccctaactc cgcccagttc    3720
cgcccattct ccgccccatg ctgactaat ttttttatt tatgcagagg ccgaggccgc    3780
ctcggcctct gagctattcc agaagtagtg aggaggcttt tttggaggcc taggcttttg    3840
caaaaagcga tcctgagaac ttcagggtga gtttggggac ccttgattgt tctttctttt    3900
tcgctattgt aaaattcatg ttatatggag ggggcaaagt tttcagggtg ttgtttagaa    3960
tgggaagatg tcccttgtat caccatggac cctcatgata tttgttc tttcactttc    4020 tactctgttg acaaccattg tctcctctta tttctttc atttctgta acttttcgt    4080 taaactttag cttgcatttg taacgaattt ttaaattcac ttttgtttat ttgtcagatt    4140
gtaagtactt tctctaatca ctttttttc aaggcaatca gggtatatta tattgtactt    4200
cagcacagtt ttagagaaca attgttataa ttaaatgata aggtagaata tttctgcata    4260
taaattctgg ctggcgtgga atattctta ttggtagaaa caactacatc ctggtcatca    4320
tcctgccttt ctctttatgg ttacaatgat atacactgtt tgagatgagg ataaaatact    4380
ctgagtccaa accgggcccc tctgctaacc atgttcatgc cttcttcttt ttcctacagc    4440
tcctgggcaa cgtgctggtt gttgtgctgt ctcatcattt tggcaaaacc ggttagtgat    4500
atcaatgaat gcaattgttg ttgttaactt gtttattgca gcttataatg gttacaaata    4560
aagcaatagc atcacaaatt tcacaaataa agcatttttt tcactgcatt ctagttgtgg    4620
tttgtccaaa ctcatcaatg tatcttatca tgtctggatc ccgggcgcag caccatggcc    4680
tgaaataacc tctgaaagag gaacttggtt aggtaccttc tgaggcggaa agaaccagct    4740
gtggaatgtg tgtcagttag ggtgtggaaa gtccccaggc tccccagcag gcagaagtat    4800
gcaaagcatg catctcaatt agtcagcaac caggtgtgga aagtccccag gctcccagc    4860 aggcagaagt atgcaaagca tgcatctcaa ttagtcagca accatagtcc gcccctaac    4920 tccgcccatc ccgcccctaa ctccgcccag ttccgcccat tctccgcccc atggctgact    4980
aatttttttt atttatgcag aggccgaggc cgcctcggcc tctgagctat tccagaagta    5040
```

```
gtgaggaggc ttttttggag gcctaggctt ttgcaaaaag ctgatcctga gaacttcagg    5100
gtgagtttgg ggaccettga ttgttctttc tttttcgcta ttgtaaaatt catgttatat    5160 ggaggggggca aagttttcag ggtgttgttt agaatgggaa gatgtccctt gtatcaccat    5220
ggaccctcat gataattttg tttctttcac tttctactct gttgacaacc attgtctcct    5280
cttattttct tttcattttc tgtaacttttt tcgttaaact ttagcttgca tttgtaacga    5340 attttttaaat tcactttttgt ttatttgtca gattgtaagt actttctcta atcacttttt    5400
tttcaaggca atcagggtat attatattgt acttcagcac agttttagag aacaattgtt    5460
ataattaaat gataaggtag aatatttctg catataaatt ctggctggcg tggaaatatt    5520
cttattggta gaaacaacta catcctggtc atcatcctgc ctttctcttt atggttacaa    5580
tgatatacac tgtttgagat gaggataaaa tactctgagt ccaaaccggg cccctctgct    5640
aaccatgttc atgccttctt cttttttccta cagctcctgg gcaacgtgct ggttgttgtg    5700
ctgtctcatc attttggcaa agtcgacgac gaacgcgtta acgttactgg ccgaagccgc    5760
ttggaataag gccggtgtgc gtttgtctat atgtgattttt ccaccatatt gccgtctttt    5820
ggcaatgtga gggcccggaa acctggcccct gtcttcttga cgagcattcc taggggtctt    5880
tcccctctcg ccaaaggaat gcaaggtctg ttgaatgtcg tgaaggaagc agttcctctg    5940
gaagcttctt gaagacaaac aacgtctgta gcgacccttt gcaggcagcg aacccccca    6000 cctggcgaca ggtgcctctg cggccaaaag ccacgtgtat aagatacacc tgcaaaggcg    6060
gcacaacccc agtgccacgt tgtgagttgg atagttgtgg aaagagtcaa atggctctcc    6120
tcaagcgtat tcaacaaggg gctgaaggat gcccagaagg taccccattg tatgggatct    6180
gatctggggc ctcggtgcac atgctttaca tgtgtttagt cgaggttaaa aaaacgtcta    6240
ggccccccga accacgggga cgtggttttc ctttgaaaaa cacgatgata at            6292
```

CELL EXPRESSION SYSTEM

TECHNICAL FIELD

The present invention relates to expression systems, in particular the invention relates to expression systems for the production of biological therapeutics.

BACKGROUND

Expression systems for the production of biological therapeutics or biopharmaceuticals, such as recombinant proteins, generally consist of a nucleic acid vector construct encoding the desired recombinant therapeutic and a chosen host cell. The vector is introduced into the host cell and the endogenous cell machinery is utilised for the production of the desired therapeutic i.e. the desired recombinant protein. The intricacies in establishing an efficient and reliable expression system for the production of approvable biological therapeutics are manifold. However, well-established expression systems may provide cost-effective alternatives for the production of pharmaceutical products otherwise difficult to obtain.

Efficiency of the system itself depends on a large variety of factors including the design of the vector and the choice of host cell. The strategic combination of regulatory elements, selection markers and stability elements within the vector sequence have to balance simple manipulation and application of the vector with high yield production of the desired biological therapeutic. Determining a cell's suitability to act as host cell in such an expression system is primarily governed by the need to maximise compatibility between the endogenous cell machinery and the regulatory elements present in the vector, while keeping potential adventitious contaminants in the final product minimal. Further, availability, cost and acceptability for regulatory approval of any therapeutic produced by the system, have to be considered.

Nucleic acid vectors used in expression systems comprise plasmids, cosmids, Yeast Artificial Chromosomes (YACs), Bacterial Artificial Chromosomes (BACs), retroviral, adenoviral and lentiviral vectors. These vectors differ in many characteristics, such as their capacity to accommodate different sized nucleic acid inserts, their most efficient introduction method into the host cell and specifically in their utilisation of the endogenous cell machineries of different types of host cells to ensure sufficient expression of the desired protein.

Regulatory elements commonly present in such expression vectors influence transcription, translation as well as protein synthesis of selection markers and of sequences encoding the desired biological therapeutic. Such regulatory elements include, but are not limited to, promoters, terminators, modifiers, insulators, spacers, regulatory protein binding sites, introns, inducers, etc.

Known promoters include constitutively active promoters such as the thymidine kinase (TK) promoter, the actin promoter, the glyceraldehyde 3-phosphate dehydrogenase (GAPDH) promoter, the simian vacuolating virus 40 (SV40) early promoter, the cyclin T1 promoter, the RNA polymerase III U3 promoter, the cyclophillin promoter, the cytomegalovirus (CMV) promoter, the *Autographa californica* nuclear polyhedrosis virus (AcNPV) P10 promoter and the β3-galactosyltransferase 5 (β3GAL-T5) promoter.

Known promoters also include inducible promoters such as the heat shock protein 70 (HSP70) promoter (stress induced), the heat shock protein 90 (HSP90) promoter (stress induced), the alcoholdehydrogenase I (alcA) promoter (alcohol induced), the activating copper-metallothionein expression (ACE1) promoter (metal induced), the small subunit of ribulose-1,5-bisphophate-carboxylase (SSU1) promoter (light induced), the hypoxia induced factor 1α (hif1α) promoter (hypoxia induced), the inducer of meiosis 2 (IME2) promoter (starvation induced), the glucocorticoid receptor (hormone induced), the estrogen receptor (hormone induced) and the ecdysone receptor (hormone induced).

Further, cell type/tissue specific promoters, such as the nkx2.5 promoter (heart cells), the islet 1 promoter (pancreatic cells), the MyoD promoter (muscle cells), the cluster of differentiation 2 (CD2) promoter (T-cells) and the collagen II promoter (cartilage), are known to change their level of activity in response to cell type specific stimuli or to progression through developmental stages.

Known terminator elements, such as the RNA Polymerase II terminator, the small nucleolar RNA 13 (snR13) terminator, the bovine growth hormone (BGH) terminator, the simian virus 40 (SV 40) terminator and the thymidine kinase (TK) terminator, may provide suitable polyadenylation signals.

Known modifier and insulator elements include the tetracycline operator/receptor (tetO/tetR) system, the upstream activating sequence of the galactose dependent GAL4 transcription factor (GAL4 UAS), the adenovirus early region B1 TATA box, binding sites for the herpes simplex virus (HSV) regulatory protein VP16, the 5'HS4 chicken β-globin insulator, the paternally expressed gene 3 (Peg3) insulator and the sea urchin arylsulfatase (ARS) gene insulator.

While many attempts have been made to establish efficient and reliable expression systems for the production of approvable biological therapeutics, problems relating to low yield and adventitious contamination of the produced biopharmaceuticals remain. Choosing the most effective combination of suitable regulatory elements from the plethora of options, such that the system conveys stability and the highest degree of compatibility with the endogenous host cell machinery, poses a major challenge in the field.

Obtaining regulatory approval for a biopharmaceutical product poses a further challenge. Regulatory approval involves determination of the safety and efficacy of the pharmaceutical product prior to marketing. The process of gaining regulatory approval for innovator drugs is very time consuming and expensive. However, once approved, these drugs may be very profitable, particularly when they are marketed under exclusivity rights such as patent protection.

The profitability of innovator drug's market may provide a substantial incentive to exploit this market once patent rights have expired. Following patent expiry, innovator drugs can be marketed as generic drugs or biosimilars for drugs produced by recombinant DNA technology. Generic versions of blockbuster biopharmaceuticals near patent expiry include Epogen (erythropoietin, EPO) and Neupogen (granulocyte colony stimulating factor, G-CSF). The approval of a follow-on version of Pfizer's Genotropin (recombinant human growth hormone) seems to indicate a change in a landscape where previously, biopharmaceuticals enjoyed immunity from competition even after expiration of their patent protection. At present, there are over 80 generic versions of biopharmaceuticals in development (Datamonitor 2010).

Biosimilars ideally are bioequivalents of the innovator drugs and, as such, the path to regulatory approval for biosimilars is in theory less arduous than for the original innovator drug as the clinical data establishing safety and efficacy have been carried out.

Approval of generic biopharmaceuticals is dependent on comparable dosage form, strength, route of administration, quality, performance characteristics and intended use compared with approved biopharmaceuticals (that is, the reference listed drugs). For example, under the United States Food and Drug Administration (FDA), approval for a generic drug involves an "Abbreviated New Drug Application" (ANDA) which generally does not include pre-clinical and clinical data to establish safety and effectiveness. Approval also involves a bioequivalence review, which establishes that the proposed generic drug is bioequivalent to the reference-listed drug. This bioequivalency is based upon a demonstration that the rate and extent of absorption of the active ingredient in the generic drug fall within the scope of the parameter of the reference listed drug.

Importantly, there is a chemistry/microbiology review process that provides an assurance that the generic drug will be manufactured in a reproducible manner under controlled conditions to ensure that the drug will perform in a safe and acceptable manner.

Although guidelines for the approval of biosimilar drugs exist, there is uncertainty in regard to the practicalities of regulatory approval of biosimilars. Much of the uncertainty is driven by the lack of a clear practical and detailed regulatory pathway for the approval of such drugs and the scientific debate over product comparability and interchangeability. The uncertainties resulting from the manufacture of biosimilar drugs under conditions different than those used by the innovator suggest that it may be impossible to develop a true "generic" version of a biotechnology drug. Indeed, regulatory authorities in Europe and the US have shunned the use of the term "biogeneric", preferring the nomenclature "biosimilar" and "follow-on biologicals".

Many quality concerns for expression system-derived biopharmaceuticals have originated from the presence of adventitious contaminants or from the properties of the host cells used to prepare the product. Several of these products have also had quality concerns regarding the expression vector of the system. It is well established that cell properties and events linked to cell culture can affect resultant product quality and safety. Effective quality control of recombinant products requires appropriate controls on all aspects of handling the cell and cell culture. This is particularly relevant to the development of biosimilars.

Previously, Chinese Hamster Ovary (CHO) cells were modified and engineered to produce insulin. However these CHO cells were unable to express biological active insulin and thus the patents associated with this type or method of CHO cell modification were not commercial exploited. Fully functional insulin was not produced in CHO cells due to cryptic splicing of the insulin gene message by the translational machinery In the CHO cell.

Any discussion of the prior art throughout the specification should in no way be considered as an admission that such prior art is widely known or forms part of common general knowledge in the field.

It is an object of the present invention to overcome or ameliorate at least one of the disadvantages of the prior art, or to provide a useful alternative.

SUMMARY

Means for Solving the Problem

A first aspect of the present invention may relates to novel expression systems and methods of employing an expression system according to the invention that may, in certain embodiments, increase the yield and decrease the cost of manufacture.

This invention relates to methods of production of recombinant biosimilars, bio-pharmaceuticals and other desirable proteins, polypeptides and peptides using mammalian cell cultures. In particular, the methods of the invention involve the use of specially bioengineered mammalian cell lines for the production of complex proteins in low cost media. These cell lines have the acquired ability for autonomous growth in cheap, reproducible, fully-defined protein-free medium, with the cells expressing and secreting its growth factor requirements.

Accordingly, in a first aspect, the present invention provides an expression system for expressing a protein comprising:
a eukaryotic host cell carrying a dihydrofolate reductase (DHFR) deficiency
an expression vector, the expression vector encoding the human growth hormone gene;
an expression vector, the expression vector comprising:
a eukaryotic selectable marker downstream of for expression of a sequence encoding dihydrofolate reductase for complementing the DHFR deficiency in the host cell;
a prokaryotic selectable marker conveying Ampicillin resistance to a prokaryotic host cell;
a prokaryotic Origin of Replication
a plurality of multiple cloning sites (MCS); and
at least one protein expression module comprising:
a Simian Vacuolating Virus 40 (SV40) early promoter, inclusive of its 72 bp enhancer repeats; and a rabbit β-globin intron sequence being separable from a SV40 polyadenylation sequence by a first multiple cloning site, for receiving a coding sequence and expressing a desired protein therefrom.

Preferably, the expression system further comprises a second protein expression module, the second protein expression module including: a Cyotomegalovirus promoter being separable from a SV40 polyadenylation sequence by a second multiple cloning site for co-expression of at least two proteins from the expression modules.

Preferably, the protein is the subject of a request for regulatory approval and wherein the host cell is subjected to a plurality of predetermined manipulations such that the host cell expresses said protein; and wherein information is recorded on each manipulation and each manipulation is carried out in a manner which prevents contact of the host cell with a contaminating agent; and wherein the information is used to generate a history record of the host cell for inclusion in a submission to a regulatory agency involved in assessing the safety and efficacy of drugs thereby expediting regulatory approval of the protein.

The predetermined manipulations preferably comprise:
(i) ligating the coding sequence encoding the desired protein into the expression vector to produce a recombinant vector;
(ii) introducing the recombinant vector into the host cell; and
(iii) culturing the host cell under conditions such that the protein is expressed by the host cell.

Preferably the recombinant vector is at least in part incorporated into the genome of the host cell. Step (iii) includes growing the host cell in a medium that contains no animal or plant derived proteins or peptides and no undefined hydolysates or lysates thereby reducing contact of the host cell with a contaminating agent.

In a particularly preferred embodiment, the host cell is a Chinese Hamster Ovary (CHO) DG44 cell.

In certain preferred embodiments, the host CHO DG44 expresses a growth hormone. In certain preferred embodiment the growth hormone is human growth hormone. In certain preferred embodiments, the protein may be a biosimilar drug.

In a second aspect, the present invention provides a method of managing the development of a protein expressed by the expression system according to the first aspect wherein the protein is the subject of a request for regulatory approval, the method comprising the steps of:
a. subjecting the host cell to a plurality of predetermined manipulations such that the cell expresses the protein;
b. recording information on each manipulation wherein each manipulation is carried out in a manner which prevents contact of the host cell with a contaminating agent;
c. using the information to generate a history record of the host cell for inclusion in a submission to a regulatory agency involved in assessing the safety and efficacy of drugs; and
d. including the history record in the submission to the regulatory agency for regulatory approval of the product.

In a third aspect, the present invention provides a method of expediting regulatory approval of a protein expressed by the expression system according to the first aspect the method comprising:
b. subjecting the host cell to a plurality of predetermined manipulations such that the host cell expresses the product;
c. recording information on each manipulation wherein each manipulation is carried out in a manner which prevents contact of the host cell with a contaminating agent;
d. using the information to generate a history record of the host cell for inclusion in a submission to a regulatory agency involved in assessing the safety and efficacy of drugs; and
e. including the history record in the submission to the regulatory agency for regulatory approval of the protein.

Preferably, step (a) of the methods according to the second and third aspect comprises
(i) ligating the coding sequence encoding the desired protein into the expression vector to produce a recombinant vector;
(ii) introducing the recombinant vector into the host cell; and
(iii) culturing the host cell under conditions such that the protein is expressed by the host cell.

The recombinant vector is preferably at least in part incorporated into the genome of the host cell.

Preferably, step (iii) of the methods according to the second and third aspect includes growing the host cell in a medium that contains no animal or plant derived proteins or peptides and no undefined hydrolysates or lysates thereby reducing contact of the host cell with a contaminating agent.

In a particularly preferred embodiment of the methods according to the second and third aspect, the protein is a biosimilar drug.

Another aspect of the present invention may also provide a method for producing a desired recombinant protein, polypeptide or peptide comprising the step of: culturing a mammalian host cell in culture medium, wherein said host cell includes:
(i) at least one introduced DNA sequence encoding a protein, polypeptide and/or peptide factor(s) required for growth of the host cell in said culture medium, expressibly linked to a constitutive promoter (e.g. CMV and SV40 promoters) The invention thereby enables the use of low cost, protein/serum-free medium by utilising a host cell which is able to produce the protein, polypeptide and/or peptide growth factor(s) required for its growth in such medium. The culture medium used in the method of the invention is, therefore, preferably serum-free or otherwise free of protein, polypeptide and/or peptide growth factor(s) necessary for the growth of the particular host cell type. However, methods wherein the culture medium includes one or more of the required growth factor(s) and the host cell itself expresses one or more of the same and/or other required growth factor(s), is also to be regarded as falling within the scope of the invention.

The mammalian host cell may be any of those commonly used in the art for expressing recombinant proteins, polypeptides or peptides. For example, the host cell may be a Chinese Hamster Ovary (CHO) cell such as CHO-K1, CHO-DG44 DHFR- and CHO-S. These include both adherent and suspension cell lines. Also other cell lines described within the embodiments of the present invention may also be used or preferred.

The introduced DNA sequence(s) may be present on plasmids or otherwise integrated into the host cell chromosomes (e.g. by homologous recombination).

The DNA sequence(s) encoding the protein, polypeptide and/or peptide factor(s) required for growth of the host cell, may be selected from DNA sequences encoding human Growth Hormone (hGH), modified hGH and other growth factors and mixtures thereof. Where the host cell is CHO it is preferable that the host cell includes DNA sequences encoding human Growth Hormone (hGH).

In the context of the present invention, the words "comprise", "comprising" and the like are to be construed in their inclusive, as opposed to their exclusive, sense, that is in the sense of "including, but not limited to".

In the context of the present invention, the words "comprise", "comprising" and the like are to be construed in their inclusive, as opposed to their exclusive, sense, that is in the sense of "including, but not limited to".

The invention is to be interpreted with reference to the at least one of the technical problems described or affiliated with the background art. The present aims to solve or ameliorate at least one of the technical problems and this may result in one or more advantageous effects as defined by this specification and described in detail with reference to the preferred embodiments of the present invention.

Figure 1A:
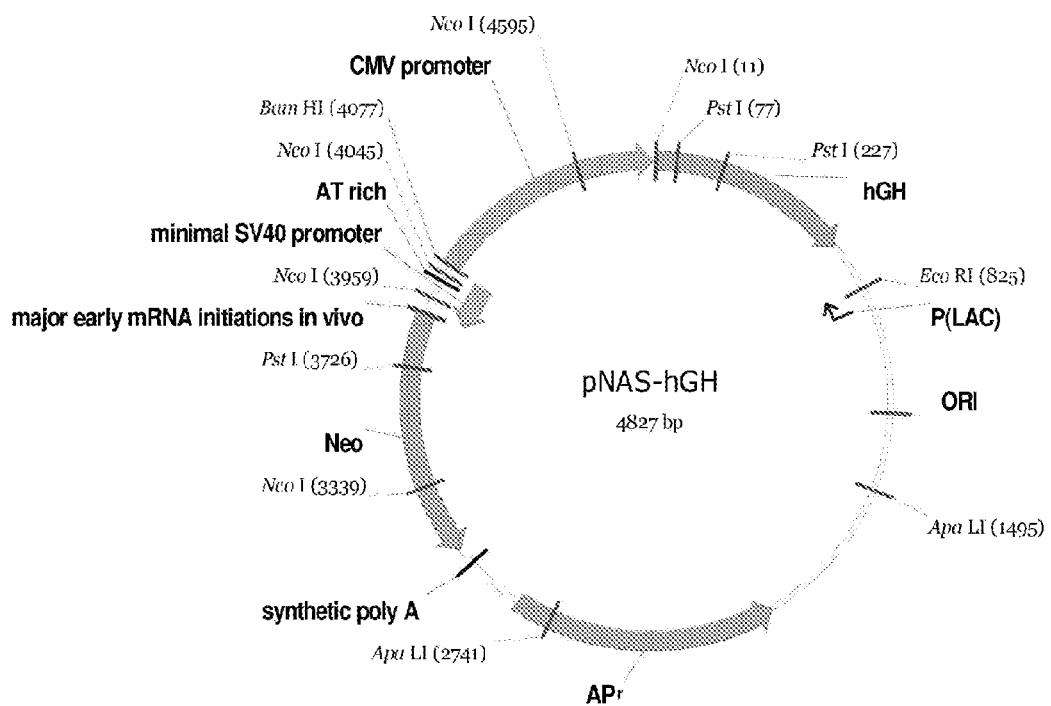
FIG. 1A is a plasmid vector map entitled pNAS-hGH for the high level expression human growth hormone (hGH) inserted within a pNAS vector with use with NeuCHO cell line.

This specification also includes the following genetic sequence information relating to expression vectors:

Sequence No. 1 depicts the preferred coding sequence for the expression vector pMAB HC;

Sequence No. 2 depicts the preferred coding sequence for the expression vector pMAB LC(ires-dhfr);

Sequence No. 3 depicts the preferred coding sequence for the expression vector pNAS-hGH;

Sequence No. 4 depicts the preferred coding sequence for the expression vector pNeu;

Sequence No. 5 depicts the preferred coding sequence for the expression vector pNeu-IRES-DHFR;

Sequence No. 6 depicts the preferred coding sequence for the expression vector pNeuMAB;

Sequence No. 7 depicts the preferred coding sequence for the expression vector pNeuMAB-IRES-DHFR (CMV);

Sequence 8 depicts the preferred coding sequence for the expression vector pNeuMAB-IRES-DHFR;

Please note that in this specification Sequence No. is same and the equivalent term to SEQ ID NO.

DESCRIPTION OF THE INVENTION

Preferred embodiments of the invention will now be described with reference to the accompanying drawings and non-limiting examples.

It has been found that events during the culture of a cell may contribute significantly to the assessment of the risks associated with the use of that particular cell for production of proteins and more particularly proteins for therapeutic use.

Diligent records of all manipulations including the history of a cell throughout development, extending to the parental cell line from which it was derived, may contribute to the quality and safety of the final product.

In one scenario, such information may be important for gaining regulatory approval of protein therapeutics expressed from a cell. In particular, biosimilars present unique issues. These issues include demonstrating that immunogenicity of the biosimilar has not been altered with respect to the reference listed drug, as well as ensuring that there are no undetected differences in the product that may potentially impact the safety and efficacy of the drug. Resolving such issues would be problematic without conducting extensive clinical trials. As such, it is likely that any application for a biosimilar would be required to demonstrate that there are no clinically meaningful differences in safety, purity and potency between the biosimilar and the reference listed drug. Moreover, an application for a biosimilar would need to provide evidence that the biosimilar has "profound similarity" (as it is impractical to demonstrate identical biological products) and that the biosimilar will produce the same clinical result as the reference listed drug in any given patient.

In order to gain regulatory approval, traditional generic manufacturers are required to demonstrate their drug is chemically identical to the referenced listed drug and exhibit the same properties in the human body as the original drug. In regard to biosimilars, it was previously not possible to readily demonstrate that a second-source biologic drug is unequivocally identical to an innovator drug due to the complexities of the synthesis of the drugs in potentially disparate biological systems. As such, biosimilars may exhibit slightly different properties to the original drugs that may necessitate abbreviated clinical trials in order to gain regulatory approval.

In the context of the present invention, the term "contaminating agent" refers to any agent that can potentially compromise regulatory approval of a product by a regulatory agency. Such agents may include but are not limited to adventitious agents such as viruses, bacteria, fungi and mycoplasma or proteins there from.

As used herein the term "cell expressed product" refers to any product produced by the cell, including but not limited to proteins, peptides, glycoproteins, carbohydrates, lipids, glycolipids and nucleic acids.

The term "regulatory approval" in so far as it relates to a product defined in the context of this specification, refers to approval from a regulatory authority which permits marketing of the product.

The term "safety and effectiveness studies" refers to any studies conducted on a product that assess the safety and efficacy of that product for human and/or animal administration.

The term "clinical trials" refers to studies involving either animal or humans designed assess the safety and/or efficacy of a product for a therapeutic application.

The term "abbreviated safety effectiveness studies and/or abbreviated clinical trials" refers to studies carried out on a drug which does not involve complete phase I, II and III clinical trials. Such studies may include a bioequivalence review and a chemistry/microbiology review as defined by the US Food and Drug Administration (FDA).

The term "biosimilar drug" and "biosimilar" refer to a bioequivalent pharmaceutical of a drug in which patent protection has expired and where the previously protected drug has regulatory approval. In particular, this includes products prepared in cell culture by recombinant DNA technology. The term "biosimilar drug" and "biosimilar" as used herein is equivalent to the terms "follow-on biologicals" or "biosimilars".

The term "protein" refers to a "complete" protein as well as fragments, derivatives or homologs or chimeras thereof comprising one or more amino acid additions, deletions or substitutions, but which substantially retain the biological activity of the complete protein.

The embodiments of the present invention will now be described by reference to the following non-limiting examples.

Example 1

Construction of pNeu and pNAS Vectors for High Level Expression of Recombinant Therapeutic Protein The vector pNeu was designed for high-level expression of single chain peptides for the production of therapeutic proteins. The vector facilitates the insertion DNA sequences into a convenient multiple cloning site for expression in CHO cells. See Table 1 and FIG. 1A for a description of the vector and its component features.

The 5026 bp vector encodes essential coding and regulatory sequences for the efficient expression of the recombinant gene as well as essential sequences for the selection and propagation of the plasmid in bacteria. It was designed for chemical synthesis and is void of nonessential and redundant sequences that are common components in commercial expression vectors. This allows for ease of genomic insertion with less likelihood of deletion of sequences during plasmid propagation resulting in loss of expression. The multiple cloning site encodes a minimum of two unique restriction sites for rapid gene cloning.

Example 2

Synthesis and Cloning of Human Growth Hormone (hGH) cDNA into pNAS

The amino acid sequence encoding for hGH was subjected to bioinformatic analysis through proprietary third party software by GENEART AG, Regensburg Germany. Codon options were utilized to maximize expression by improving mRNA maintenance and the exploitation of available tRNA pools in CHO cells. RNA and codon optimization was performed on the coding sequences. The gene was analysed with respect to splice site recognition, mRNA stability, presence of ribosomal entry sites, mRNA secondary structures, self-homology for the purpose of increasing gene expression in CHO cells. The hGH gene was cloned into pNAS using AgeI and EcoRV restriction sites using methods well known in the art.

Example 3

Construction of pNeuMAB Vector for Expression of Recombinant Monoclonal Antibody The pNeuMAB vector was designed for the cloning and expression of recombinant monoclonal antibodies. The DNA encoding heavy and light chains are configured in the vector as two distinct and tandem transcription units. See Table 1 and FIG. 1B for a description of the vector and its component features.

Synthesis of cDNA Encoding Heavy Chain and Light Chain of an Antibody—Infliximab The amino acid sequence encoding the heavy chain (HC) and light chain (LC) of the monoclonal antibody, Infliximab were subjected to bioinformatic analysis through proprietary third party software by GENEART AG, Regensburg Germany. Codon options were utilized to maximize expression by improving mRNA maintenance and the exploitation of available tRNA pools in CHO cells. RNA and codon optimization was performed on the coding sequences. The genes were analysed with respect to splice site recognition, mRNA stability, presence of ribosomal entry sites, mRNA secondary structures, self-homology for the purpose of increasing gene expression in CHO cells.

Cloning Gene Encoding Heavy Chain of Infliximab

The synthetic gene encoding for the heavy chain of Infliximab was assembled from synthetic oligonucleotides and/or PCR products. The fragment was cloned into pGA14 (ampR) using AscI and PacI restriction sites. The plasmid DNA was purified (Pure Yield™ Plasmid Midiprep, Promega) from transformed bacteria and concentration determined by UV spectroscopy. The final construct was verified by sequencing. The sequence congruence within the used restriction sites was 100%. The synthetic cDNA sequence encoding heavy chain of Infliximab was designed to incorporate unique restriction sites Age I and Eco RV at the 5' and 3' ends respectively for directional cloning into the first multiple cloning site of NeuClone's antibody expression vector, pNeuMAB digested with the same restriction sites.

Cloning Gene Encoding Light Chain of Infliximab

The synthetic gene encoding the light chain of Infliximab was assembled from synthetic oligonucleotides and/or PCR products. The fragment was cloned into pGA18 (ampR) using AscI and PacI restriction sites. The plasmid DNA was purified (Pure Yield™ Plasmid Midiprep, Promega) from transformed bacteria and concentration determined by UV spectroscopy. The final construct was verified by sequencing. The sequence congruence within the used restriction sites was 100%. The synthetic cDNA sequence encoding light chain of Infliximab incorporates the unique restriction sites Sal I and Mlu I at the 5' and 3' ends respectively for directional cloning into the second multiple cloning site of NeuClone's antibody expression vector, pNeuMAB digested with the same restriction sites.

Generation of NeuCHO

Transfection of DG44 Cells with pNAS-hGH

One of the preferred methods by which the expression vector encoding human growth hormone into the host CHO DG44 cell line and the status of the rDNA within the host (copy number, etc.) is as follows. Briefly, a total of $1.5 \times 10e7$ cells were transfected with 1.8 ug of linearized plasmid DNA together with 15 ul of FreeStyle MAX Reagent (Invitrogen) in a volume of 30 ml. The transfected cell cultures were incubated at 37 C, 8% CO2 on an orbital shaker platform. At 48 hours post transfection the cells were cultured in hypoxanthine- and thymidine-deficient, medium supplemented with Gentamycin at a final concentration of 500 ug/ml for selection of uptake of plasmid DNA. Clones were selected by limiting dilution cloning. Several single clones arising from a single cell were expanded and cell lines were characterised for production of human growth hormone. Resulting clones were examined for growth properties in comparison to the standard CHO DG44 cell line.

Transfection of NeuCHO with pNeuMAB Encoding Infliximab Genes

Linearized plasmid pNeuMAB DNA encoding Infliximab genes was used to transfect NeuCHO cell cultures At 48 hours post transfection the cells were cultured into hypoxanthine- and thymidine-deficient, medium to select for cells expressing the DHFR gene. A stable cell population was then subjected to subsequent stepwise increasing methotrexate (MTX) concentration (50-, 100-, 200-, 400-, 800 nM, 1 uM) in order to amplify template DNA copy number and gene expression. Clones were selected by limiting dilution cloning. Clones with high level expression of infliximab protein were scaled up for protein production.

Example 4

Cell Banking

A critical part of quality control involves the full characterization of cells. The cell banks are examined for adventitious agents (viral, bacterial, fungal and mycoplasmal). Documentation describing the type of banking system used, the size of the cell bank(s) the container (vials, ampoules and closure system used, the methods used for preparation of the cell bank(s) including the cryoprotectants and media used, and the conditions employed for cryopreservation and storage are provides.

The procedures used to avoid microbial contamination and cross-contamination by other cell types present in the laboratory, and the procedures that allow the cell bank containers to be traced are all made available. This includes a description of the documentation system as well as that of a labelling system which can withstand the process of preservation, storage, and recovery from storage without loss of labelling information on the container.

It is essential that production is based on a well-defined master and working cell bank system. During the establishment of the banks no other cell lines are handled simultaneously in the same laboratory suite or by the same persons. The origin, form, storage, use and expected duration at the anticipated rate of use are described in full for all cell banks.

The following table identifies some of the components and features of the various expression vectors using with either CHO DG44 or NeuCHO cell lines. The data has been divided into three tables for purposes of presentation in this patent specification.

TABLE 1

| Feature | pNeu | pNeu-IRES-DHFR | pNAS | pNeuMAB |
|---|---|---|---|---|
| Multiple cloning site | One multiple cloning site for insertion of expression unit coding for single chain protein | One multiple cloning site for insertion of expression unit coding for single chain protein | One multiple cloning site for insertion of expression unit coding for single chain protein | Two multiple cloning sites for insertion of expression units coding for heavy and light chains of a monoclonal antibody |
| Strong promoter/ enhancer combination | The SV40 virus early promoter/ enhancer | The SV40 virus early promoter/ enhancer | The CMV early promoter/ enhancer drives expression of each transcription unit | The SV40 virus early promoter/ enhancer drives expression of the first and 2nd transcription unit |
| Intron/ intervening sequence | The intron sequence II from rabbit beta globin gene is located downstream of the promoter providing for increased expression and mRNA stability of the transcription unit | The intron sequence II from rabbit beta globin gene is located downstream of the promoter providing for increased expression and mRNA stability of the transcription unit | | The intron sequence II from rabbit beta globin gene is located downstream of the promoter providing for increased expression and mRNA stability of the first transcription unit |
| Intenal Ribosome Entry Site (IRES) | | For the expression of DHFR gene downstream of $2^{nd}$ transcription unit ensuring high level expression of $2^{nd}$ cistron in cells growing in the presence of methotrexate | | |
| Polyadenylation signal | A strong polyadenylation signal from S40 virus for efficient expression of recombinant gene. | A strong polyadenylation signal from S40 virus for efficient expression of recombinant gene. | A strong polyadenylation signal from S40 virus for efficient expression of recombinant gene | A strong polyadenylation signal from S40 virus is for efficient expression of each recombinant gene |
| DHFR gene | Auxotrophic selection in HT negative media eliminates the need to maintain selection pressure using antibiotics. Amplification of gene copy | Auxotrophic selection in HT negative media eliminates the need to maintain selection pressure using antibiotics. Amplification of gene copy | | Auxotrophic selection in HT negative media eliminates the need to maintain selection pressure using antibiotics. Amplification of gene copy number is |

TABLE 1-continued

| Feature | pNeu | pNeu-IRES-DHFR | pNAS | pNeuMAB |
|---|---|---|---|---|
| | number is accomplished by the addition of methotrexate to the culture media. The murine DHFR gene is driven by a minimal SV40 early promoter lacking the enhancer sequence. | number is accomplished by the addition of methotrexate to the culture media. The murine DHFR gene is driven by a minimal SV40 early promoter lacking the enhancer sequence. | | accomplished by the addition of methotrexate to the culture media. The murine DHFR gene is driven by a minimal SV40 early promoter lacking the enhancer sequence |
| Ampicillin resistance gene | For propagation of plasmid in bacteria | For propagation of plasmid in bacteria | For propagation of plasmid in bacteria | For propagation of plasmid in bacteria |
| Neomycin gene | | | For selection in mammalian cells | |

TABLE 2

| Features | pNeuMAB-IRES-DHFR | pNeuMAB-IRES-DHFR(CMV) | pMAB-LC (ires-dhfr) |
|---|---|---|---|
| Multiple cloning site | Two multiple cloning sites for insertion of expression units coding for heavy and light chains of a monoclonal antibody | Two multiple cloning sites for insertion of expression units coding for heavy and light chains of a monoclonal antibody | One multiple cloning site for insertion of Light chain gene |
| Strong promoter/enhancer combination | The SV40 virus early promoter/enhancer drives expression of the first and 2nd genes | The SV40 virus early promoter/enhancer drives expression of the first gene and the CMV promoter drives expression of the $2^{nd}$ gene. | The SV40 virus early promoter/enhancer drives expression of LC gene |
| Intron/intervening sequence | The intron sequence II from rabbit beta globin gene is located downstream of the promoter providing for increased expression and mRNA stability of the transcription unit | The intron sequence II from rabbit beta globin gene is located downstream of the promoter providing for increased expression and mRNA stability of the transcription unit | The intron sequence II from rabbit beta globin gene is located downstream of the promoter providing for increased expression and mRNA stability of the transcription unit |
| Intenal Ribosome Entry Site (IRES) | For the expression of DHFR gene downstream of $2^{nd}$ transcription unit ensuring high level expression of $2^{nd}$ cistron in cells growing in the presence of methotrexate | For the expression of DHFR gene downstream of $2^{nd}$ transcription unit ensuring high level expression of $2^{nd}$ cistron in cells growing in the presence of methotrexate | For the expression of DHFR gene downstream of $2^{nd}$ transcription unit ensuring high level expression of $2^{nd}$ cistron in cells growing in the presence of methotrexate |
| Polyadenylation signal | A strong polyadenylation signal from S40 virus for efficient expression of recombinant | A strong polyadenylation signal from S40 virus for efficient expression of recombinant gene. | A strong polyadenylation signal from S40 virus for efficient expression of recombinant gene. |

TABLE 2-continued

| Features | pNeuMAB-IRES-DHFR | pNeuMAB-IRES-DHFR(CMV) | pMAB-LC (ires-dhfr) |
|---|---|---|---|
| DHFR gene | gene. Auxotrophic selection in HT negative media eliminates the need to maintain selection pressure using antibiotics. Amplification of gene copy number is accomplished by the addition of methotrexate to the culture media. The murine DHFR gene is driven by a minimal SV40 early promoter lacking the enhancer sequence. | Auxotrophic selection in HT negative media eliminates the need to maintain selection pressure using antibiotics. Amplification of gene copy number is accomplished by the addition of methotrexate to the culture media. The murine DHFR gene is driven by a minimal SV40 early promoter lacking the enhancer sequence. | Auxotrophic selection in HT negative media eliminates the need to maintain selection pressure using antibiotics. Amplification of gene copy number is accomplished by the addition of methotrexate to the culture media. The murine DHFR gene is driven by a minimal SV40 early promoter lacking the enhancer sequence. |
| Ampicillin resistance gene | For propagation of plasmid in bacteria | For propagation of plasmid in bacteria | For propagation of plasmid in bacteria |
| Neomycin gene | | | |

TABLE 3

| Features | pMAB-HC |
|---|---|
| Multiple cloning site | One multiple cloning site for insertion of Heavy chain gene. Vector is similar to pNAS |
| Strong promoter/enhancer combination | The CMV early promoter/enhancer drives expression of heavy chain gene |
| Intron/intervening sequence | |
| Intenal Ribosome Entry Site (IRES) | |
| Polyadenylation signal | A strong polyadenylation signal from S40 virus for efficient expression of recombinant gene. |
| DHFR gene | |
| Ampicillin resistance gene | |
| Neomycin gene | For selection in mammalian cells |

FIG. 1 A-H depicts a series of expression vector map relevant to expression using CHO DG44 cell lines or NeuCHO cell lines.

More specifically, FIG. 1A depicts an expression vector pNAS including hGH coding sequence for use in constructing the NeuCHO Cell Line from CHO DG44. Preferably, NeuCHO cell line is produced by the inclusion of the vector shown in FIG. 1A within a CHO-DG44 cell line. The genetic sequence for this expression vector has been submitted along with this application and is designated SEQ. ID No. 1.

It is noted that CHO DG44 cell line includes a relatively and fragile cell line which inherently has issues and problems in regard to long term viability, cell density and population stability.

In this preferred embodiment, the addition of hGH to the cell culture vector may lead to increases in cell density or production that were previously not realisable using previous techniques and sequences. Previously, growth factors such as IGF-1 and insulin were used to supplement CHO cells (such as DG44). However these previous methods lead to disappointing results in terms of cell viability and/or survival. In the present embodiments, the addition of hGH coding sequences to CHO cells allows for the excretions by the CHO-DG44 cells of hGH. This expression and secretion of hGH into the cell media leads to increase in cell survival of CHO cells.

Further the expression of hGH may also improve the robustness of the NeuCHO cell line as compared to other CHO cell lines.

More specifically, the addition of hGH expressing sequences to CHO-DG44 cells gave rise to a new cell line, NeuCHO cell line. The NeuCHO cell line may include any of the expression vectors described and shown in respect to FIGS. 1 A-H.

The NeuCho cell line, deposited under the provisions of the Budapest Treaty with the Cell Bank Australia located at 214 Hawkesbury Rd, Westmead, NSW, 2145, Australia as of 4 Feb. 2013 and assigned accession no. CBA20130024, as is particularly suitable for use in pharmaceutical manufacture as described within the present application.

Preferably, the CHO-DG44 cell line was transfected with the pNAS-hGH vector to produce the NeuCHO cell line. Possible transfection methods include: standard methods described in the scientific literature including: calcium phosphate precipitation, PEI, Electroporation and lipofaction. It is generally noted that previous teachings in the field have often argued that it is preferred to deliver higher relative levels of DNA to cells by transfection to get better results. However, transfection methods delivering more DNA into the cell do not generate more stable or high producing cell lines, as the cell lines may become less stable and less robust.

Figure 1B:
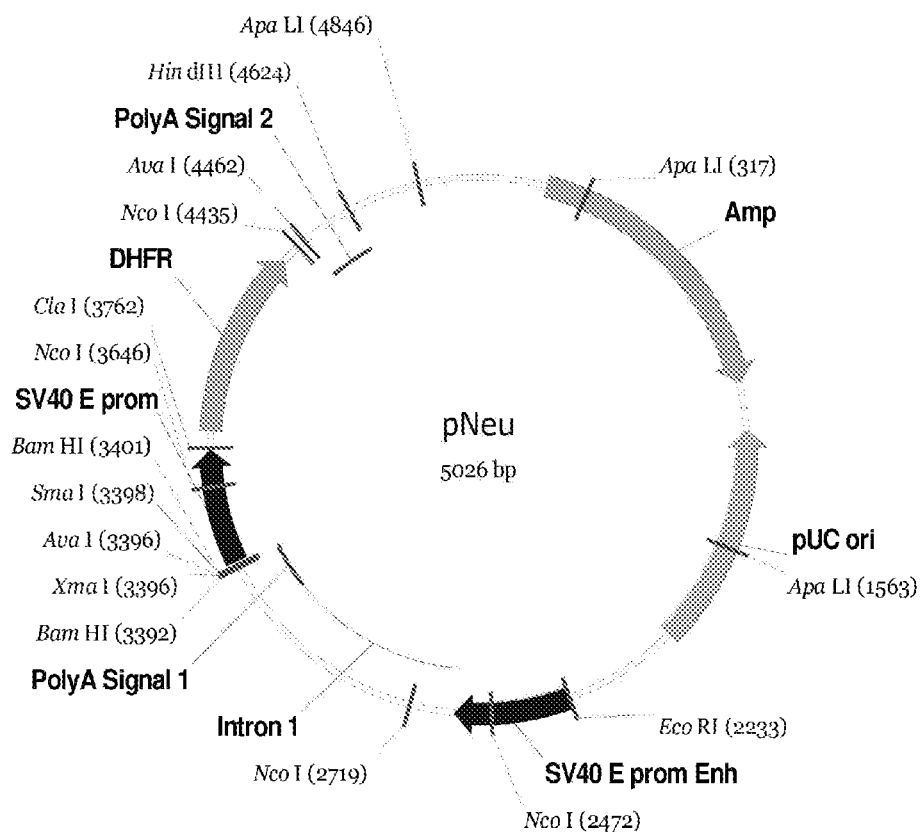
FIG. 1B is an expression vector map entitled "pNeu" used for the high level expression of a single chain protein in CHO DG44 cells.

FIG. 1B depicts an expression vector used for the expression of a single chain protein in CHO DG44 cells. Preferably, the recombinant gene expression may be driven by the SV40 early promoter/enhancer within the vector. The genetic sequence for this expression vector has been submitted along with this application and is designated SEQ. ID No. 2.

Figure 1C:
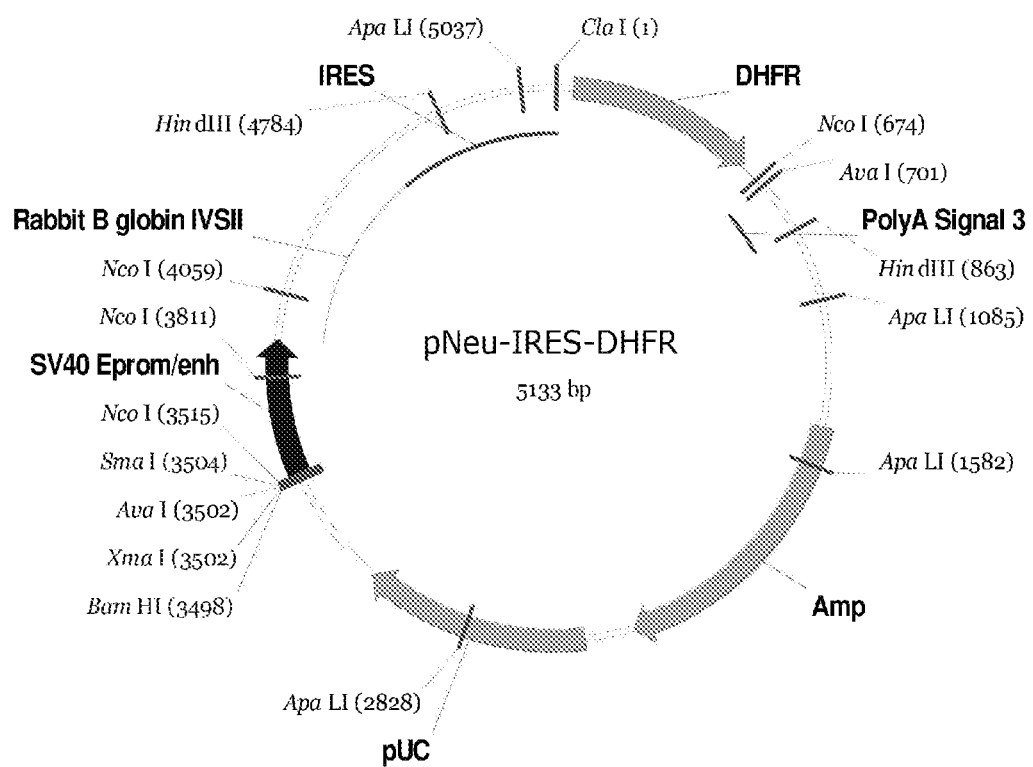
FIG. 1C is an expression vector map entitled "pNeu-IRES-DHFR" used for the high level expression of a single chain protein in CHO DG44 cells. A dicistronic expression cassette with recombinant gene in $1^{st}$ cistron followed by DHFR gene in $2^{nd}$ cistron.

FIG. 1C depicts an expression vector used for the expression of a single chain protein in CHO DG44 cells. Preferably, a dicistronic expression cassette with a recombinant gene in the $1^{st}$ cistron followed by a DHFR gene in the $2^{nd}$ cistron is described in this example. The gene expression in this vector is preferably driven by SV40 early promoter or enhancer. The genetic sequence for this expression vector has been submitted along with this application and is designated SEQ. ID No. 3.

Figure 1D:
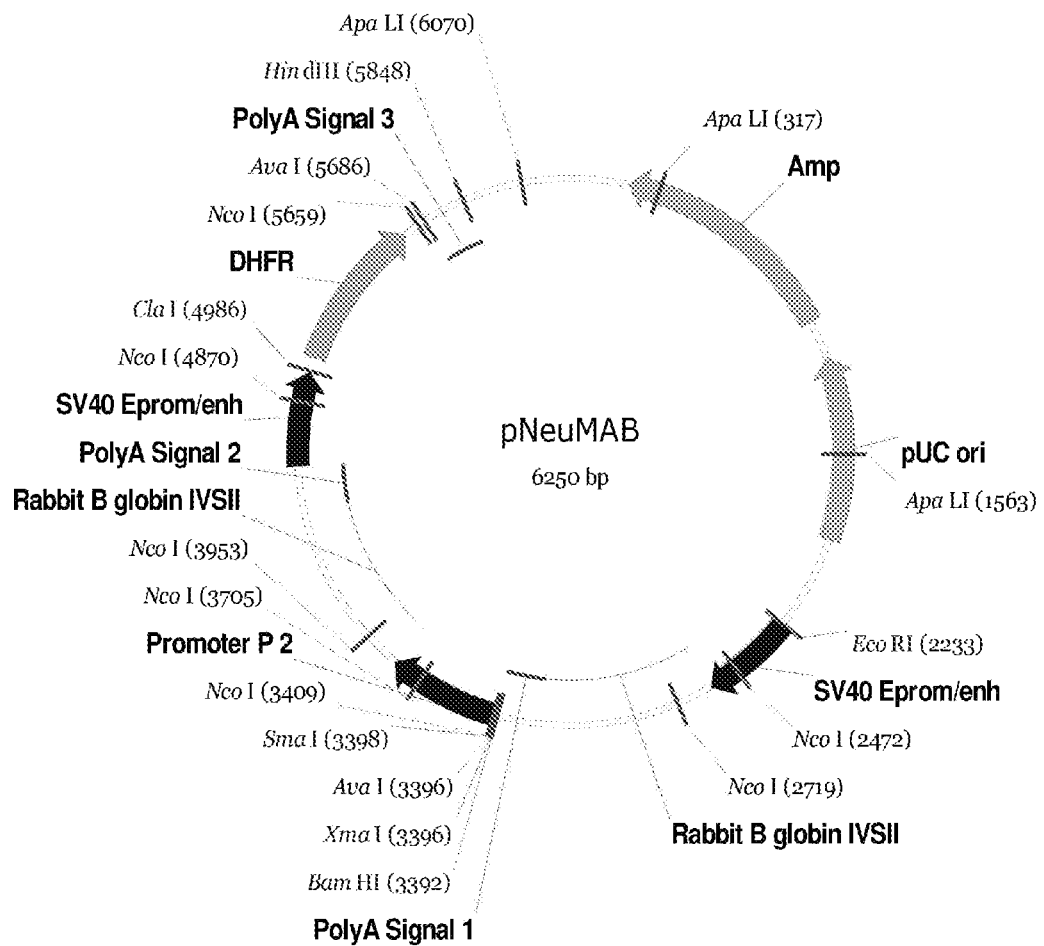
FIG. 1D is an expression vector map entitled "pNeuMAB" used for the high level expression of heavy and light antibody chains and/or recombinant monoclonal antibodies.

FIG. 1D depicts a pNeuMAB, which is a dual expression vector containing two cloning cassettes to insert heavy and light chain genes into a single vector. This expression vector has two gene expression cassettes for the insertion of multiple recombinant genes. Each cassette includes an SV40 early promoter and downstream poly A sequence. Each gene is driven by driven SV40 promoter without an enhancer sequence. This expression vector is suitable for expression of light and heavy chains expression of the antibodies. The genetic sequence for this expression vector has been submitted along with this application and is designated SEQ. ID No. 4.

Figure 1E:
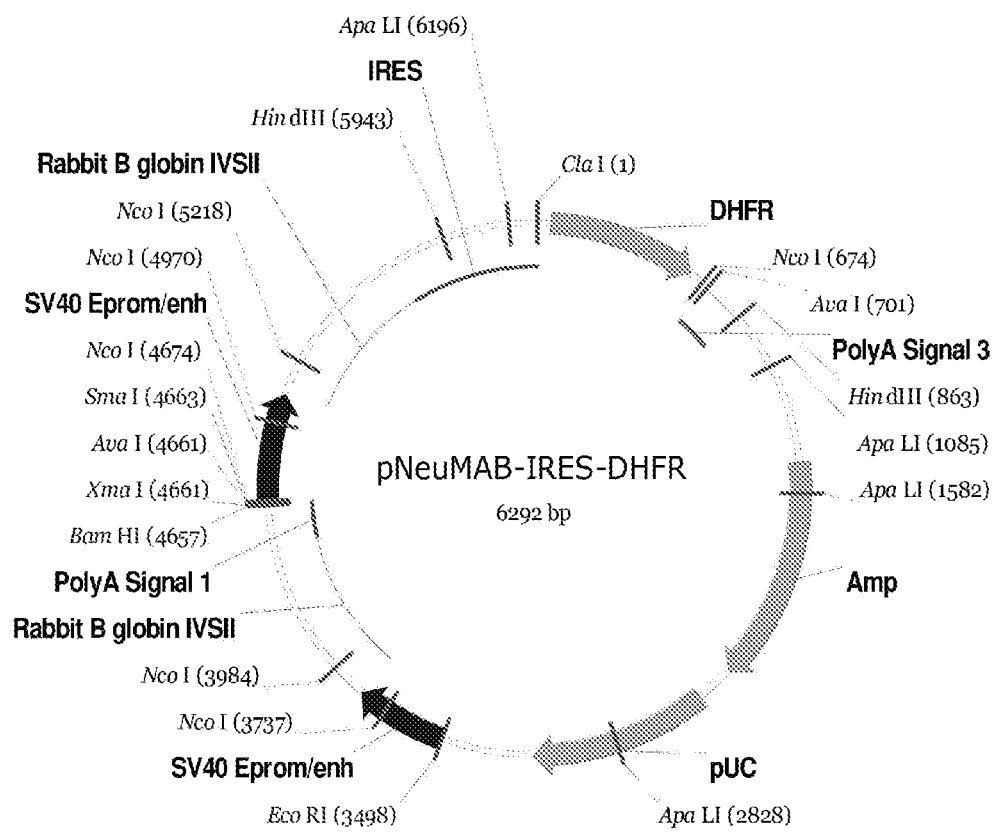
FIG. 1E is an expression vector map entitled "pNeuMAB-IRES-DHFR" used for the high level expression of heavy and light antibody chains.

FIG. 1E depicts a further expression vector, pNeuMAB-IRES-DHFR, for high level expression of heavy and light chains of a recombinant monoclonal antibody on a single vector driven one SV40 promoter and enhancer. This expression vector may be used for the expression of light and heavy antibody chains. This expression vector generally includes two gene expression cassettes for insertion of recombinant genes. Each cassette consists of SV40 early promoter/enhancer and downstream poly A sequence. Heavy chain and light chain are inserted in 1st and 2nd cassettes respectively. The 2nd cassette is dicistronic having light chain followed by DHFR downstream of IRES. The genetic sequence for this expression vector has been submitted along with this application and is designated SEQ. ID No. 5.

Figure 1F:
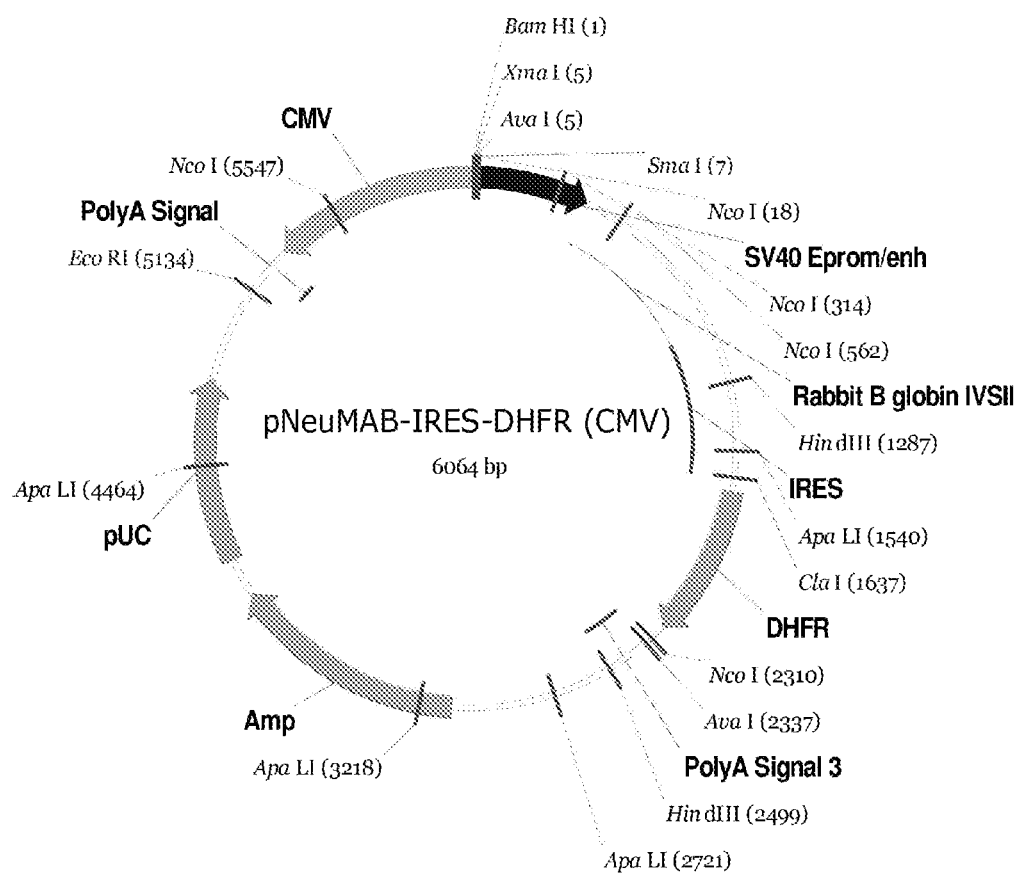
FIG. 1F is an expression vector map entitled "pNeuMAB-IRES-DHFR (CMV)" used for the high level expression of heavy and light antibody chains.

FIG. 1F depicts a further expression vector, pNeuMAB-IRES-DHFR-(CMV), for high level expression of heavy and light chains of recombinant monoclonal antibody on a single vector driven by CMV and SV40 promoters of heavy and light chains of antibodies respectively. The DHFR gene is driven by IRES downstream of light gene; for the expression of heavy and light chains of antibody in opposite orientations with respect to each other. Heavy chain is driven by CMV promoter whereas light chain is driven by SV40 promoter/enhancer. Light chain and DHFR gene have a dicistronic configuration with DHFR downstream of IRES. The genetic sequence for this expression vector has been submitted along with this application and is designated SEQ. ID No. 6.

Figure 1G:
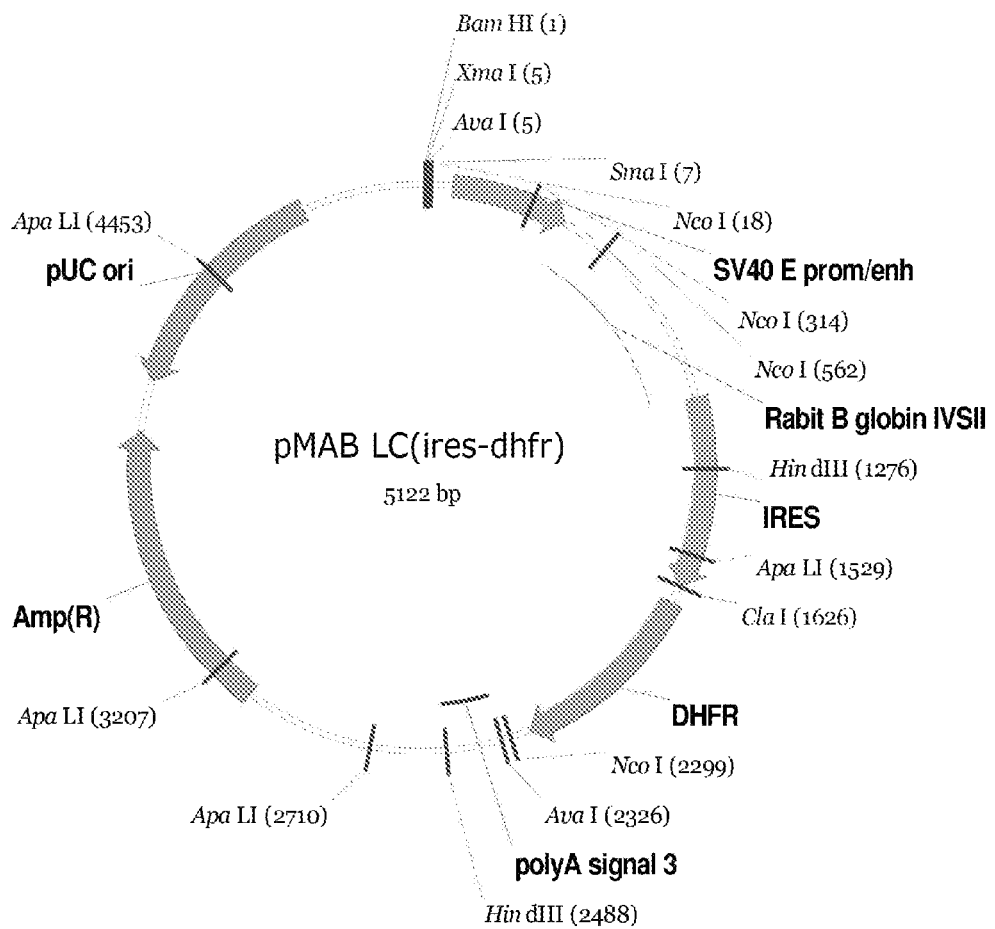
FIG. 1G is a single chain expression vector map entitled "pMAB LC (IRES-DHFR)" used for expression of light chains (LC)

FIG. 1G depicts a further expression vector, pMAB-LC (ires-dhfr), for expression of only light chains (LC) of antibodies. A discistronic cassette for cloning LC in 1st cistron and DHFR in 2nd cassette downstream of IRES. The vector is used in co-transfection with pMAB HC, which is the expression vector shown in FIG. 1H. The genetic sequence for this expression vector has been submitted along with this application and is designated SEQ. ID No. 7.

Figure 1H:
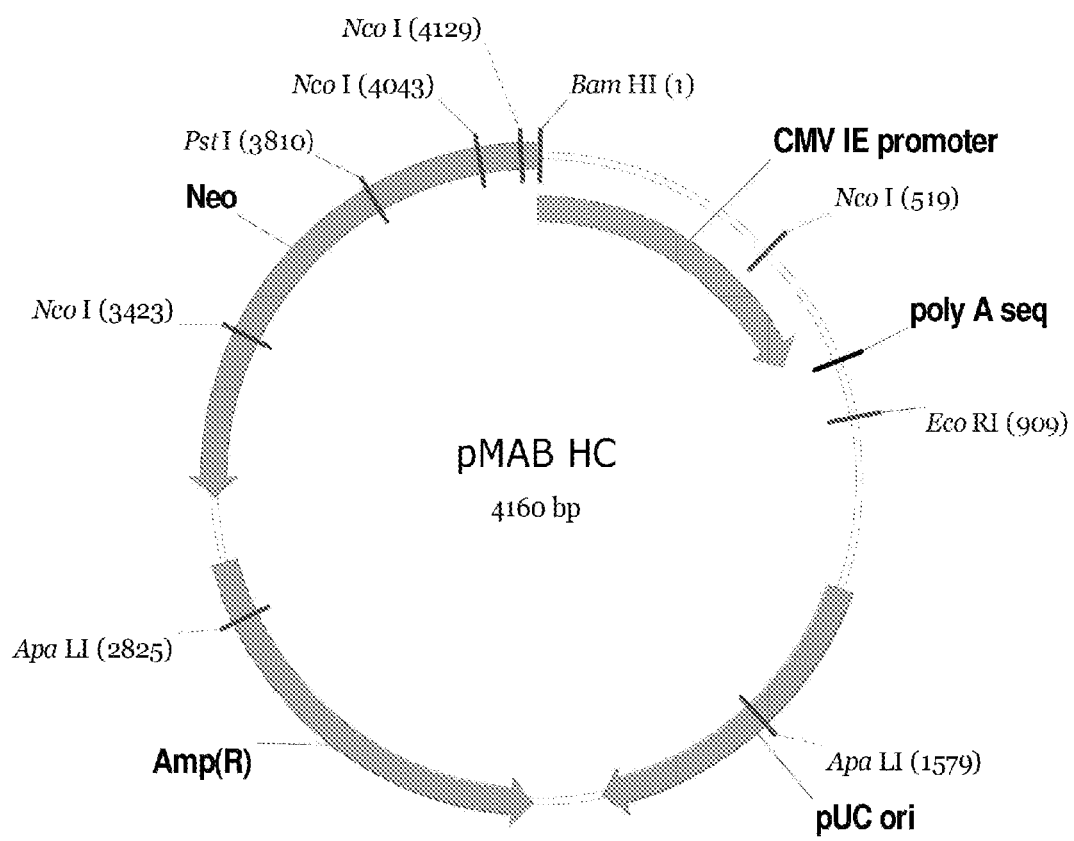
FIG. 1H is a single chain expression vector map entitled "pMAB HC" used for expression of heavy chains (HC)

FIG. 1H depicts a further expression vector, pMAB-HC, for expression of only heavy chain (HC) of antibodies. Both pMAB-LC and pMAb-HC are co-transfected for expression of complete antibody. The genetic sequence for this expression vector has been submitted along with this application and is designated SEQ. ID No. 8.

Figure 2:
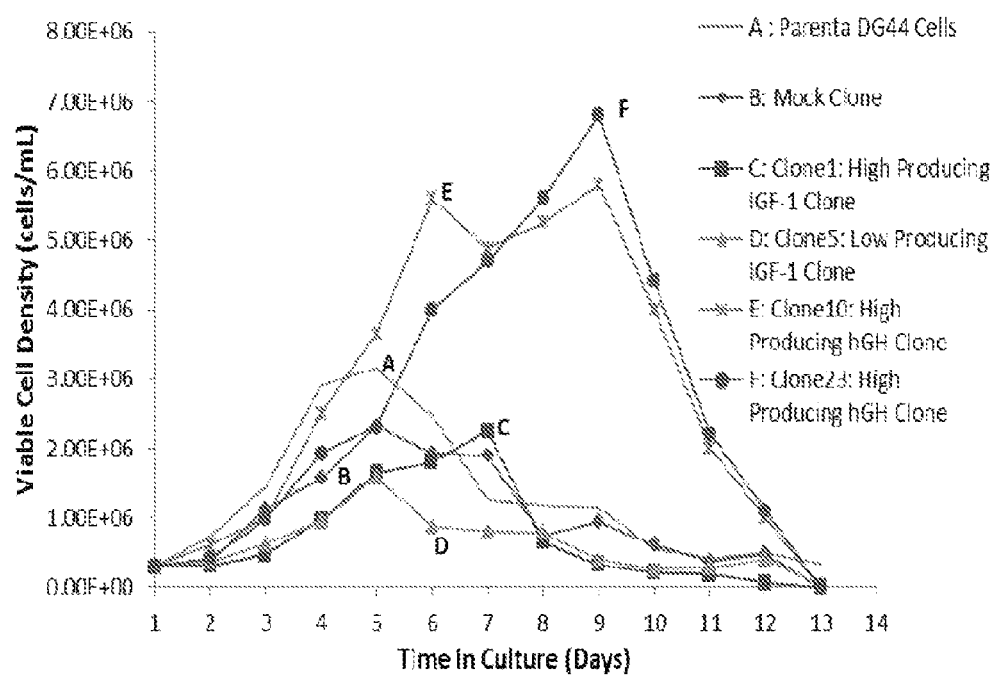
FIG. 2. depicts a growth chart demonstrating viable cell density plotted against time in respect of various cultures and cells used. Growth of DG44 Cell Lines expressing hGH compared to the Parental DG44 Cell Line and a DG44 Cell Line expressing the IGF-1 gene.

A further graph is shown in FIG. 2. The graph of FIG. 2 represents the: Growth of DG44 Cell Lines expressing IGF-1 or hGH compared to the Parental DG44 Cell Line and a Mock Cell Line. A control (mock) cell line is derived from the Parental Cell Line which has been stably transfected with a DNA plasmid containing the selection marker but without the Gene Of Interest (GOI).

The preferred NeuCHO Cell Line demonstrates superior growth advantage compared to the original Parental DG44 Cell Line. In this example, the growth of NeuCHO cells demonstrates higher viable cell densities to that of a DG44 Cell Line expressing the IGF-1 gene.

This graph shows that when DG44 cells express human Growth Hormone, (Line Graphs E and F), the cells have a very high Maximum Viable Cell Density (up to 425%) compared to the untransfected DG44 Parental Cell Line, the Mock transfected Cell Line, and DG44 Cell Lines expressing high or Low IGF-1 protein.

The NeuCHO Cell Line has an Integral Cell Density of up to $3.67 \times 10^7$ cell/day/mL, which is 230% that of the Parental DG44 Cell Line, $1.57 \times 10^7$ cell/day/mL.

Also in FIG. 2, the Viable Cell Density is plotted on the Y-axis in cells/mL, and the number of days in culture is plotted on the X-axis. Six line graphs are shown in the figure, namely line graph A, B, C, D, E and F.

Line A represents the growth pattern of a parental DG44 cell line that is not transfected with DNA.

Line B represents the growth pattern of a parental DG44 cell line that was transfected with a DNA plasmid containing the selection marker but without the Gene Of Interest (GOI).

Line C represents the growth pattern of a parental DG44 cell line that was stably transfected with a DNA plasmid containing both the selection marker and the Gene Of Interest (GOI). The GOI here is Insulin-like growth factor 1 (IGF-1).

Line D represents the growth pattern of a parental DG44 cell line that was stably transfected with a DNA plasmid containing both the selection marker and the Gene Of Interest (GOI). The GOI here is Insulin-like growth factor 1 (IGF-1).

Line E represents the growth pattern of a parental DG44 cell line that was stably transfected with a DNA plasmid containing both the selection marker and the Gene Of Interest (GOI). The GOI here is human Growth Hormone (hGH).

Line F represents the growth pattern of a parental DG44 cell line that was stably transfected with a DNA plasmid containing both the selection marker and the Gene Of Interest (GOI). The preferred GOI in this example is human Growth Hormone (hGH).

Figure 3:
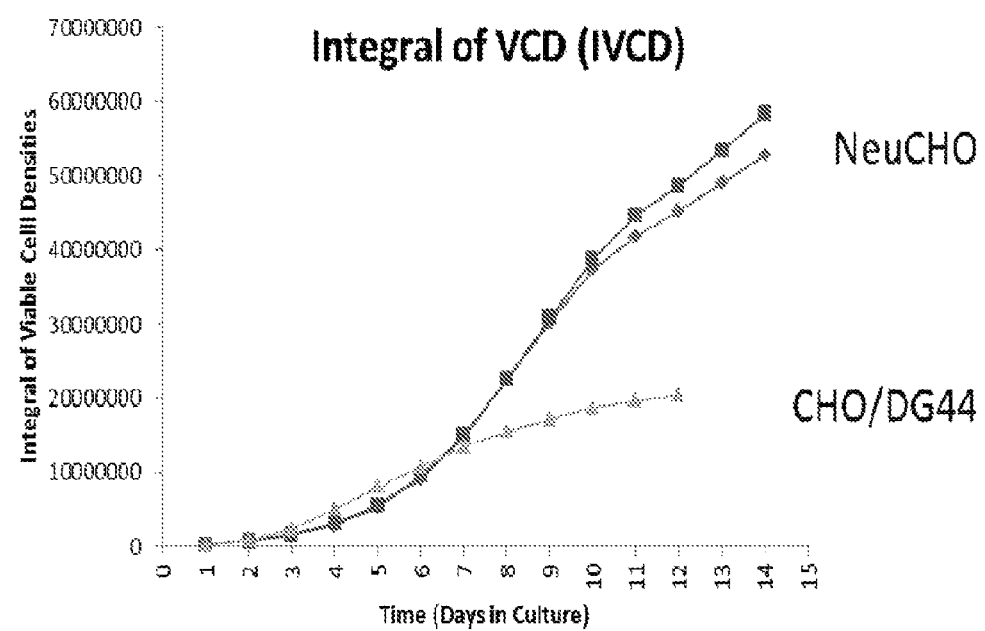
FIG. 3. depicts a graph comparing the integral of viable cell densities against time for various preferred organisms and culture.
Figure 4:
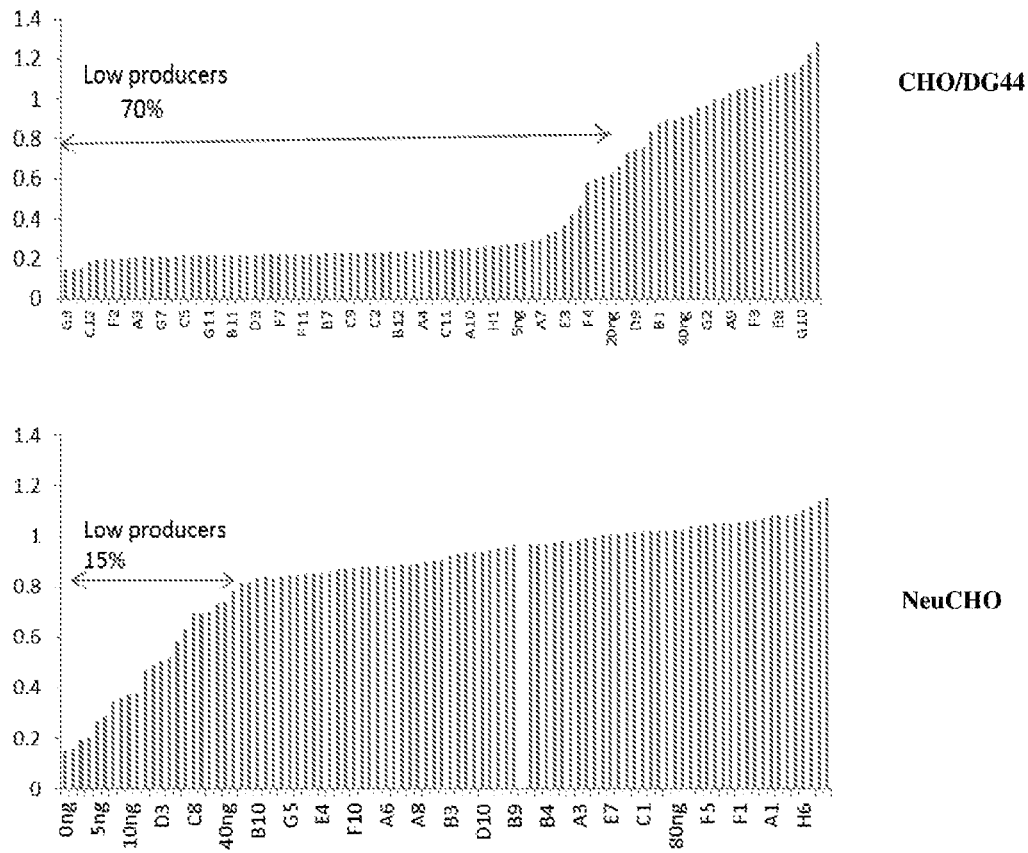
FIG. 4. depicts a comparison chart showing the relative expression levels of proteins from either CHO DG44 cells or NeuCHO cell lines.

In FIG. 3, a further graph is depicted comparing the integral of viable cell densities (IVCD) of NeuCHO with the standard CHO DG44 cells. This figure demonstrates the difference in the Integral of Viable Cell Densities achieved with the parent cell line NeuCHO compared to parental CHO.

The NeuCHO cell line is superior in growth capabilities and this translates into a more efficient production process which can minimize costs by having higher productions rates, fewer production runs, thus lower productions costs, lower Cost of Goods (COGS).

Growth and productivity of NeuCHO cell line expressing a recombinant mAB.

The preferred NeuCHO cell line demonstrates high titre of mAB x compared to traditional CHO expression system.

FIG. 5 demonstrates in graphical form that NeuCHO cells may have greater stable transfection efficiency than CHO cells (such CHO DG44 cells). Cells (NeuCHO and CHO) were transfected with DNA encoding mAB 'x' prior to selection and single cell cloning from a stable pool. The data is shown in FIG. 5 and demonstrates that stable transfection of NeuCHO cells results in a greater number of clones with high productivity than that of standard CHO cells. The graph shows the levels of various protein expressed in relative quantities at a given time.

NeuCHO cells have an integral of viable cell density that is about 230% greater than CHO DG44 cell lines. CHO DG44 cell lines expressing insulin like growth factor 1 (IGF-1) do not demonstrate the ability to grow to high cell densities as NeuCHO cell lines may generally achieved. NeuCHO cells have a generally greater transfection efficiency than CHO DG44 cells. The survival rate of transfected NeuCHO cells is generally greater then transfected CHO DG44 cells. Additionally, transfection of NeuCHO cells may result in a greater number of clones with a higher productivity than that of standard CHO DG44 cells.

Preferably, the expression system and vectors described herein may be able to allow or facilitate CHO cells such NeuCHO or CHO DG44 cells to produce desired proteins suitable for pharmaceutical preparation including, but not limited to: Infliximab tumour necrosis factor (referred to as Remicab™); Adalimumab tumour necrosis factor (referred to as Humira™); Etanercept tumour necrosis factor (referred to as Enbrel™); Rituximab CD20 (referred to as Rituxan™ & MabThera™); Bevacizumab vascular endothelial growth factor (referred to as Avastin™); Trastuzumab HER2 (referred to as Herceptin™); Ranibizumab vascular endothelial growth factor (referred to as Lucentis™); Cetuximab epidermal growth factor receptor (referred as Erbitux™); Erythropoietin α; Interferon α—Pegylated interferon alfa-2a; Interferon α—Pegylated interferon alfa-2b and hGH.

NeuCHO cells when used as feeder layer may also increase efficiency of single cell cloning. NeuCHO cells were seeded in single wells of microtitre plates prior to single cell cloning of a stable transfected pool. Secretion of human growth hormone secreted from NeuCHO cells results in an increased survival rate of single cells following Limiting Dilution Cloning.

Although the invention has been described with reference to specific examples, it will be appreciated by those skilled in the art that the invention may be embodied in many other forms, in keeping with the broad principles and the spirit of the invention described herein.

The present invention and the described preferred embodiments specifically include at least one feature that is industrial applicable.

The claims defining the invention are as follows:

1. A method for producing a desired recombinant polypeptide comprising culturing a mammalian host cell expressing a desired recombinant polypeptide in the presence of a human Growth Hormone (hGH) or modified hGH, wherein the mammalian host cell co-expresses the hGH or modified hGH and the desired recombinant polypeptide, and wherein expression of the hGH or modified hGH enhances survival and/or cell density and/or cell viability of the mammalian host cell expressing the desired recombinant polypeptide.

2. The method according to claim 1, wherein the hGH is constitutively expressed in the mammalian host cell.

3. The method according to claim 1, wherein the mammalian host cell is a CHO cell.

4. The method according to claim 3, wherein the CHO cell is selected from the group consisting of: a CHO-K1, a CHO-DG44 and a CHO-S cell.

5. The method according to claim 1, wherein culturing is performed in a suspension culture.

6. The method according to claim 1, wherein culturing is performed in an adherent culture.

7. The method according to claim 1, wherein the desired recombinant polypeptide is a biosimilar of a recombinant protein.

8. The method according to claim 7, wherein the recombinant protein is selected from the group consisting of: Infliximab, Adalimumab, Etanercept, Rituximab, Bevacizumab, Trastuzumab, Ranibizumab, Cetuximab, Erythropoietin alpha, Interferon alpha, Interferon alpha 2a and Interferon alpha 2b.

9. The method according to claim 1, wherein the expression of the hGH or modified hGH increase cell density and viability of the host mammalian cell compared to the mammalian cell supplemented with insulin-like growth factor 1 (IGF-1).

10. A recombinant mammalian host cell for producing a desired recombinant polypeptide, wherein a mammalian host cell co-expresses:
   i) a human Growth Hormone (hGH) or modified hGH, and
   ii) a desired recombinant polypeptide,
   wherein expression of the hGH or modified hGH enhances survival of the mammalian host cell and wherein the desired recombinant polypeptide is selected from the group consisting of: Infliximab, Adalimumab, Etanercept, Rituximab, Bevacizumab, Trastuzumab, Ranibizumab, Cetuximab, Erythropoietin alpha, Interferon alpha, Interferon alpha 2a and Interferon alpha 2b.

11. The recombinant mammalian host cell according to claim 10 wherein the hGH is constitutively expressed in the mammalian host cell.

12. The recombinant mammalian host cell according to claim 10, wherein the mammalian host cell is a CHO cell.

13. An expression system for producing a desired recombinant polypeptide comprising:
   an expression vector comprising a nucleotide sequence encoding a human Growth Hormone (hGH) or modified hGH;
   an expression vector comprising a nucleotide sequence encoding a desired recombinant polypeptide; and a mammalian host cell used to co-express the hGH or modified hGH and the desired recombinant polypeptide.

14. The expression system according to claim 13, wherein the mammalian host cell is a CHO cell.

15. The expression system according to claim 14, wherein the CHO cell is selected from the group consisting of: a CHO-K1, a CHO-DG44 and a CHO-S cell.

16. The expression system according to claim 15, wherein the CHO cell has a dihydrofolate reductase (DHFR) deficiency.

17. The expression system according to claim 13, wherein the desired recombinant polypeptide is a biosimilar of a recombinant protein.

18. The expression system according to claim 17, wherein the recombinant protein is selected from the group consisting of: Infliximab, Adalimumab, Etanercept, Rituximab, Bevacizumab, Trastuzumab, Ranibizumab, Cetuximab, Erythropoietin alpha, Interferon alpha, Interferon alpha 2a and Interferon alpha 2b.

19. The expression system of claim 17, wherein the recombinant protein is selected from the group consisting of: an antibody that binds tumour necrosis factor, an antibody that binds to a vascular endothelial growth factor, an antibody that binds to HER2, and an antibody that binds to an epidermal growth factor receptor.

* * * * *